United States Patent [19]

Saikawa et al.

[11] 4,200,744
[45] Apr. 29, 1980

[54] SUBSTITUTED 7α-METHOXY-7β[(2,3-DIOXO-1-PIPERAZINYL)CARBONYLAMINO-PHENYLACETAMIDO]CEPHALOSPORINS

[75] Inventors: Isamu Saikawa; Shuntaro Takano; Hiroyuki Imaizumi; Isamu Takakura; Hirokazu Ochiai; Takashi Yasuda; Hideo Taki; Masuru Tai; Yutaka Kodama, all of Toyama, Japan

[73] Assignee: Toyama Chemical Company, Limited, Tokyo, Japan

[21] Appl. No.: 845,935

[22] Filed: Oct. 27, 1977

Related U.S. Application Data

[63] Continuation-in-part of Ser. No. 759,134, Jan. 13, 1977, Pat. No. 4,129,730.

[30] Foreign Application Priority Data

Jul. 21, 1977 [JP] Japan ................................. 52-86613
Jul. 21, 1977 [JP] Japan ................................. 52-87540

[51] Int. Cl.² ............................................ C07D 501/36
[52] U.S. Cl. ................................... 544/21; 424/246
[58] Field of Search ....................................... 544/21

[56] References Cited

U.S. PATENT DOCUMENTS

| 3,956,292 | 5/1976 | Cooper | 544/27 |
| 4,045,438 | 8/1977 | Havig et al. | 544/21 |
| 4,087,424 | 5/1978 | Saikawa et al. | 260/268 C |
| 4,103,008 | 7/1978 | Toshiyasu et al. | 544/27 |
| 4,129,730 | 12/1978 | Saikawa et al. | 544/21 |

FOREIGN PATENT DOCUMENTS 51-113890 10/1976 Japan ..

*Primary Examiner*—Donald G. Daus
*Assistant Examiner*—David E. Wheeler
*Attorney, Agent, or Firm*—Oblon, Fisher, Spivak, McClelland & Maier

[57] ABSTRACT

Novel 7α-methoxy-cephalosporins and non-toxic salts thereof, which contain a di-oxo-piperazinyl-carbonylamino group in molecule. These compounds are valuable antibacterial compounds for use in mammals including man. This disclosure relates to such compounds and methods for producing the same.

12 Claims, No Drawings

SUBSTITUTED 7α-METHOXY-7β[(2,3-DIOXO-1-PIPERAZINYL)-CARBONYLAMINOPHENYLACETAMIDO]CEPHALOSPORINS

CROSS-REFERENCES TO RELATED APPLICATIONS

This application is a continuation-in-part of application Ser. No. 759,134 filed Jan. 13, 1977, now U.S. Pat. No. 4,129,730.

This invention relates to novel 7α-methoxy-cephalosporins and method for producing the same.

7α-Methoxy-cephalosporins hitherto disclosed have an antibacterial activity against Gram-positive bacteria. However, they are known to have no effective antibacterial activity against Gram-negative bacteria, particularly *Pseudomonas aeruginosa* which causes clinically serious infectious diseases.

The present inventors conducted intensive studies with the aim of obtaining a compound which has so broad an antibacterial spectrum as to show an effective activity even against *Pseudomonas aeruginosa* and is resistant to the action of cephalosporinase. As the result, there have been discovered novel 7α-methoxy-cephalosporins fully satisfying the above-mentioned requirements.

It is an object of this invention to provide novel 7α-methoxy-cephalosporins which have a broad antibacterial spectrum against Gram-positive and Gram-negative bacteria, are resistant to the action of cephalosporinase and, at the same time, are effective to human and animal diseases.

It is another object of this invention to provide a process for producing said novel 7α-methoxy-cephalosporins.

Other objects and advantages of this invention will become apparent from the following description.

The novel 7α-methoxy-cephalosporins of this invention are represented by the general formula [I]:

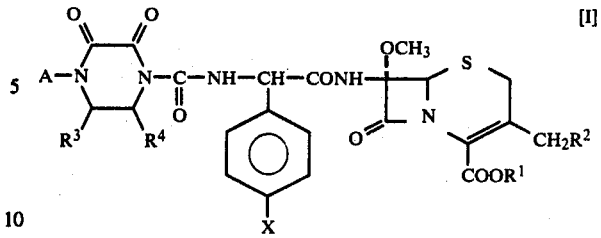

wherein $R^1$ is a hydrogen atom, a blocking group (that is, a protective group) or a salt-forming cation; $R^2$ is a hydrogen atom or an organic group linked through O or S; $R^3$ and $R^4$ are independently a hydrogen atom or a lower alkyl group; A is a substituted or unsubstituted alkyl group; and X is a hydrogen atom or a hydroxyl group.

The compounds of this invention are characterized in that an α-methoxy substituent is attached to the 7-position of the cephem ring and a group represented by the formula,

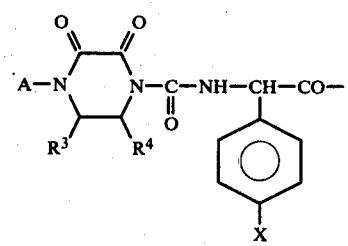

wherein $R^3$, $R^4$, A and X are as defined above, is attached to the amino group in the 7-position.

Among the compounds represented by the general formula [I], excellent are those represented by the formula [Ia], particularly those represented by the formula [Ib], and more particularly those represented by the formulae [Ic] and [Id].

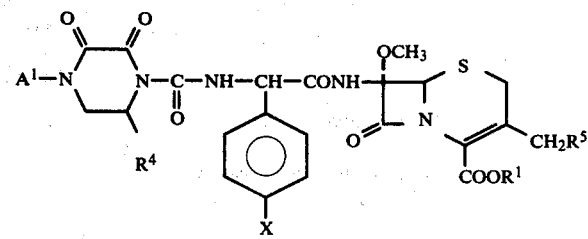

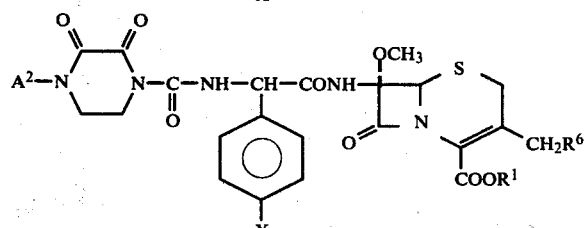

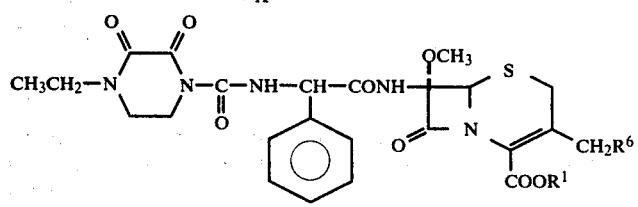

-continued

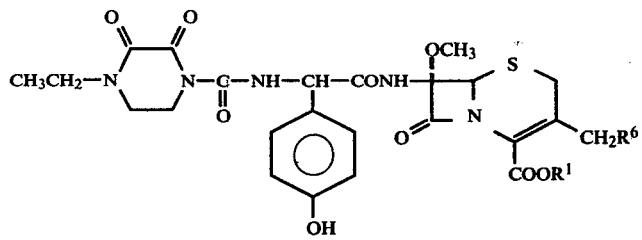
[Id]

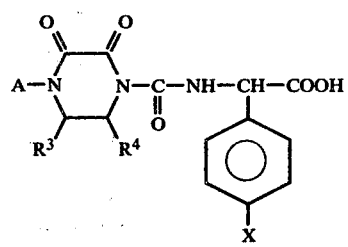
[V]

wherein $A^1$ is a lower alkyl group; $A^2$ is a methyl or ethyl group; $R^5$ is an acetoxy, carbamoyloxy, 5-(1-methyl-1,2,3,4-tetrazolyl)thio, 2-(5-methyl-1,3,4-thiadiazolyl)thio, 5-(1,2,3-triazolyl)thio, alkylthio having 1 to 4 carbon atoms or methoxy group; $R^6$ is an acetoxy, carbamoyloxy, 5-(1-methyl-1,2,3,4-tetrazolyl)thio or 2-(5-methyl-1,3,4-thiadiazolyl)thio group; and $R^1$, $R^4$ and X are as defined above.

The 7α-methoxy-cephalosporins of this invention can be produced by one of the processes described below:

1. Process (1)

This process comprises reacting a compound [II] represented by the general formula [II]:

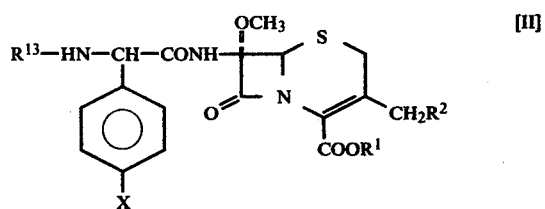
[II]

wherein X, $R^1$ and $R^2$ are as defined above and $R^{13}$ is a hydrogen atom, an organic silyl group or an organic phosphorus-containing group, with a reactive derivative in the carboxyl group of a compound [III] represented by the general formula [III]:

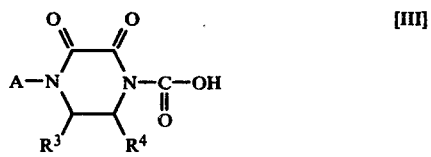
[III]

wherein A, $R^3$ and $R^4$ are as defined above.

2. Process (2)

This process comprises reacting a compound [IV] represented by the general formula [IV]:

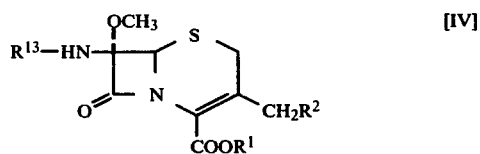
[IV]

wherein $R^1$, $R^2$ and $R^{13}$ are as defined above, with a compound [V] represented by the general formula [V]:

wherein $R^3$, $R^4$, A and X are as defined above, or a reactive derivative in the carboxyl group of the compound.

3. Process (3)

This process comprises reacting a compound [VI] represented by the general formula [VI]:

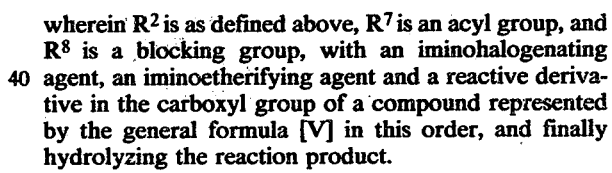
[VI]

wherein $R^2$ is as defined above, $R^7$ is an acyl group, and $R^8$ is a blocking group, with an iminohalogenating agent, an iminoetherifying agent and a reactive derivative in the carboxyl group of a compound represented by the general formula [V] in this order, and finally hydrolyzing the reaction product.

4. Process (4)

This process comprises reacting a compound [VII] represented by the general formula [VII]:

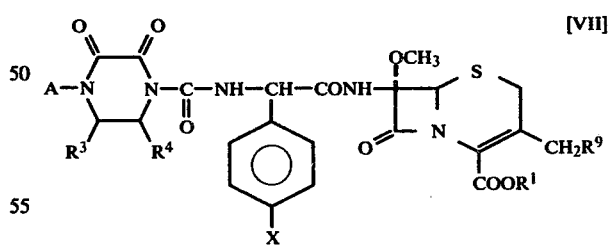
[VII]

wherein $R^1$, $R^3$, $R^4$, A and X are as defined above and $R^9$ is a substituent readily replaceable with a nucleophilic reagent, with a compound [VIII] represented by the general formula [VIII]:

$R^{10}M$ [VIII]

wherein $R^{10}$ is an organic group which is linked through O or S and M is a hydrogen atom, an alkali metal or an alkaline earth metal, to produce a compound [I'] represented by the general formula [I']:

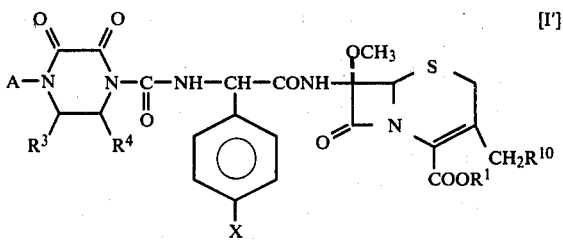

5. Process (5)

This process comprises eliminating the blocking group from a compound [IX] represented by the general formula [IX]:

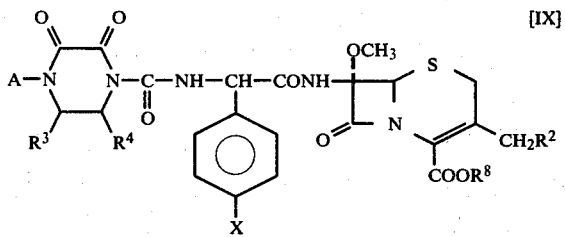

wherein $R^2$, $R^3$, $R^4$, $R^8$, A and X are as defined above.

6. Process (6)

This process comprises reacting a compound [X] represented by the general formula [X]:

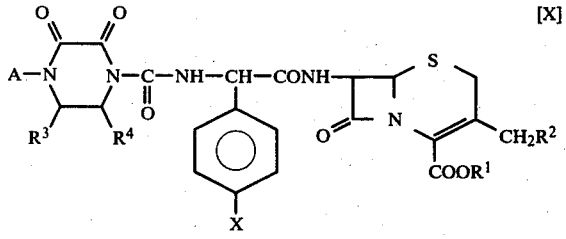

wherein A, $R^1$, $R^2$, $R^3$, $R^4$ and X are as defined above, with a compound [XI] represented by the general formula [XI] in the presence of methanol:

$$CH_3O^{-+}M^1 \qquad [XI]$$

wherein $M^1$ is an alkali metal, and then reacting the reaction product thus obtained with a halogenating agent.

The terms "blocking group," "non-toxic salt" and "salt-forming cation" used herein mean those conventionally used in the field of penicillins and cephalosporins. Concrete examples of the blocking group include the followings:

(A) Ester-forming groups capable of being eliminated by catalytic reduction, chemical reduction or other treatments under mild conditions, for example, substituted arylsulfonylalkyl groups such as p-toluenesulfonylethyl and the like; substituted or unsubstituted aralkyl groups such as benzyl, 4-nitrobenzyl, diphenylmethyl, trityl, 3,5-di(tert.-butyl)-4-hydroxybenzyl and the like; benzoyloxymethyl group; substituted or unsubstituted alkyl groups such as tert.-butyl, trichloroethyl and the like; phenacyl groups; and alkyloxyalkyl groups such as methoxymethyl and the like.

(B) Ester-forming groups capable of being eliminated readily in living bodies by the action of enzyme, for example, acyloxyalkyl groups such as pivaloyloxymethyl and the like; phthalidyl group; indanyl group; and the like.

(C) Organic silyl groups, organic phosphorus-containing groups and organic tin-containing groups capable of being eliminated readily by a treatment with water or an alcohol, for example, $(CH_3)_3Si-$; $(CH_3)_2Si<$;

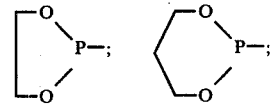

$(C_2H_5O)_2P-$; $(C_2H_5)_2P-$; $(C_4H_9)_3Sn-$; and the like.

Examples of said non-toxic salt include alkali metal salts such as sodium salt, potassium salt and the like; alkaline earth metal salts such as calcium salt, magnesium salt and the like; ammonium salt; and salts with nitrogen-containing organic bases such as procaine, dibenzylamine, N-benzyl-$\beta$-phenethylamine, 1-ephenamine, N,N'-dibenzylethylenediamine and the like.

Examples of said salt-forming cation include not only those cations which can form the aforesaid non-toxic salts, but also those cations which can form salts with other nitrogen-containing organic bases such as trimethylamine, triethylamine, tributylamine, pyridine, dimethylaniline, N-methylpiperidine, N-methylmorpholine, diethylamine, dicyclohexylamine and the like.

Concrete examples of said organic group linked through O or S which can be used as $R^2$ in this invention include alkyloxy groups such as methoxy, ethoxy, propoxy, butoxy and the like; alkylthio groups such as methylthio, ethylthio, propylthio, butylthio and the like; acyloxy groups such as acetoxy, propionyloxy, butyryloxy, benzoyloxy, naphthoyloxy, cyclopentanecarbonyloxy, cyclohexanecarbonyloxy, furoyloxy, thenoyloxy and the like; carbamoyloxy groups; and heterocyclic thio groups which contain at least one hetero atom selected from O, S and N in any combination in any position or positions, such as oxazolylthio, thiazolylthio, isoxazolylthio, isothiazolylthio, imidazoylthio, pyrazolylthio, pyridylthio, pyrazinylthio, pyrimidinylthio, pyridazinylthio, quinolylthio, isoquinolylthio, quinazolylthio, indolylthio, indazolylthio, oxadiazolylthio, thiadiazolylthio, triazolylthio, tetrazolylthio, triazinylthio, benzimidazolylthio, benzoxazolylthio, benzthiazolylthio, triazolopyridylthio, purinylthio, pyridine-1-oxide-2-ylthio and the like. Those groups which are derived from the above-mentioned groups usable as $R^2$ by replacing their hydrogen atoms with various substituents such as halogen atoms, hydroxyl groups, alkyl groups, alkyloxy groups having 1 to 5 carbon atoms, hydroxylalkyl groups having 1 to 5 carbon atoms, alkylthio groups having 1 to 5 carbon atoms, alkylamino groups having 1 to 5 carbon atoms, dialkylamino groups having 1 to 5 carbon atoms in each alkyl, acylamino groups having 2 to 5 carbon atoms, acyl groups having 2 to 5 carbon atoms, acyloxy groups having 2 to 5 carbon atoms, N,N-dialkylaminoalkyl groups having 1 to 5 carbon atoms in each alkyl, alkyloxyalkyl groups having 1 to 5 carbon atoms in each alkyl, carboxyalkyl groups having 2 to 6 carbon atoms, sulfoalkyl groups having 1 to 5 carbon atoms, sulfamoylalkyl groups having 1 to 5 carbon atoms, carbamoylalkyl groups having 1 to 5 carbon atoms, aryl groups such as phenyl, naphthyl or the like, nitro groups, cyano groups, carboxyl groups, carbamoyl groups, sulfo groups, sulfamoyl groups, and the like are also included.

The term "alkyl group" used herein means straight or branched chain alkyl groups having 1 to 13 carbon atoms, such as methyl, ethyl, propyl, isopropyl, butyl, pentyl, hexyl, heptyl, octyl, dodecyl and the like. The term "lower alkyl group" used herein means straight chain alkyl groups having 1 to 4 carbon atoms. As the substituents in the "substituted alkyl groups," there may be used, various substituents such as halogen atoms, for example, chlorine and bromine; hydroxyl group; alkyloxy groups having 1 to 5 carbon atoms; alkylthio groups having 1 to 5 carbon atoms, nitro group; cyano group; carboxyl group; acyl groups having 2 to 5 carbon atoms and the like.

Acyl group $R^7$ may be any of the acyl groups drived from aliphatic, aromatic, aralphatic, alicyclic or heterocyclic compounds, among which an acyl group represented by the following general formula is particularly preferable:

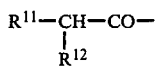

wherein $R^{11}$ is an alkyl group such as methyl, ethyl, propyl, butyl or the like; an aralkyl group such as benzyl, phenethyl or the like; an aryl group such as phenyl or the like; an aryloxy group such as phenoxy, naphthoxy or the like; or a γ-(substituted amino)-γ-carboxypropyl group such as γ-N-ethoxycarbonylamino-γ-carboxypropyl, γ-N-phenylcarbamoylamino-γ-carboxypropyl or the like; $R^{12}$ is a hydrogen atom; a hydroxyl group; a halogen atom, such as chlorine or bromine; or a lower alkyl group such as methyl, ethyl or propyl; and each of the groups usable as $R^{11}$ or $R^{12}$ may have various substituents such as halogen atom, hydroxyl group, nitro group, alkyl group, alkyloxy group having 1 to 5 carbon atoms, or the like.

Concrete examples of the substituent $R^9$ which can readily be replaced with a nucleophilic reagent include halogen atoms such as chlorine, bromine and the like; lower alkanoyloxy groups such as formyloxy, acetoxy, propionyloxy, butyryloxy, pivaloyloxy and the like; arylcarbonyloxy groups such as benzoyloxy, naphthoyloxy and the like; arylcarbonylthio groups such as benzoylthio, naphthoylthio and the like; carbamoyloxy group; and heterocyclic aromatic amine-N-oxide-thio groups in which the thio group is attached to the carbon atom adjacent to the N-oxide group in the molecule, such as pyridine-1-oxide-2-ylthio, pyridazine-1-oxide-6-ylthio and the like. Also, the above $R^9$ groups may have a substituent such as a halogen atom, for example, chlorine, bromine or the like; a nitro group; an alkyl groups; an alkoxy group having 1 to 5 carbon atoms; or the like.

$R^{13}$ represents an organic silyl group or an organic phosphorus-containing group capable of being eliminated readily by a treatment with water or an alcohol, for example, $(CH_3)_3Si-$; $(CH_3)_2Si<$;

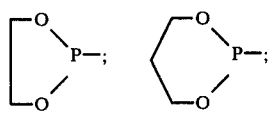

$(C_2H_5O)_2P-$; $(C_2H_5)_2P-$; and the like.

In case X is a hydroxyl group in the starting compounds [II], [V] or [X] used in Processes (1), (2), (3) and (6) the hydroxyl group may be blocked by the abovementioned organic silyl group or organic phosphorus-containing group.

$R^{10}$ represents an organic group linked through O or S. Examples of the organic group linked through O include alkyloxy groups such as methoxy, ethoxy, propoxy, butoxy, and the like. Examples of the organic group linked through S include the groups mentioned in respect of $R^2$.

Examples of M include hydrogen atom, alkali metals such as sodium, potassium and the like and alkaline earth metals such as calcium, magnesium and the like.

$M^1$ represents an alkali metal such as lithium, sodium, potassium and the like.

The compounds represented by formula [V] can be obtained according to the following reactions:

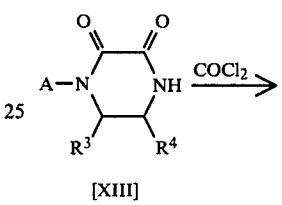

[XIII]

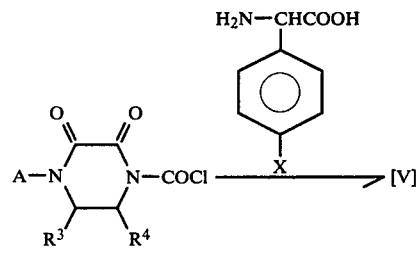

[XIV]

wherein the starting compound 2,3-dioxopiperazine is obtainable according to the process described in J. Org. Chem. 15, 68–73 (1950).

The reactive derivatives in the carboxyl group of the compound of formula [V] are those usually employed for the synthesis of acid amide, such as acid halides, acid anhydrides, mixed acid anhydrides with organic or inorganic acids, active amides, active esters and the like. Concrete examples of said reactive derivative include acid chlorides, acid cyanides and acid azides of the compound of formula [V]; mixed acid anhydrides of the compound of formula [V] with other acids such as aliphatic carboxylic acids, aromatic carboxylic acids, alkylcarbonic acids, aralkylcarbonic acids, dialkylphosphoric acids, diphenylphosphoric acids, methanesulfonic acid, p-toluenesulfonic acid and the like; acid amides of the compound of formula [V] with imidazole, 4-substituted imidazoles, dimethylpyrazole, triazole, tetrazole, saccharin and the like; and esters of the compound of formula [V] such as cyanomethyl ester, substituted phenyl esters, substituted phenyl thioesters and the like.

Examples of the reactive derivative in the carboxyl group of the compound of formula [III] are the same as those of the reactive derivative in the carboxyl group of the compound of formula [V], among which acid halides and active esters are particularly preferable. They can be obtained, for example, by treating a compound of the general formula [XIII] with phosgene or trichloromethyl chloroformate, or the like.

Among the compounds represented by the general formula [IV], 3-(substituted methyl)-7β-amino-7α-methoxy-Δ³-cephem-4-carboxylic acid can be obtained, for example, by reducing benzhydryl 7-azido-7-methoxycephalosporanate with hydrogen in the presence of platinum oxide according to the procedure described in J.A.C.S., 94, 1408 (1972) or by eliminating 4-hydroxy-3,5-di-tert.-butylbenzylidene group from 7β-(4-hydroxy-3,5-di-tert.-butylbenzylideneamino)-7α-methoxy-3-(substituted methyl)-Δ³-cephem-4-carboxylate by the usual method as described in Tetrahedron Letter, 2705–8 (1975).

The compounds represented by formulas [II] and [VI] can be obtained by acylating the compound of the general formula [IV] in the usual manner or by the method described in J. Org. Chem. 39, 2795 (1974); J. Org. Chem., 38, 943–949 (1973).

The compounds of the general formulas [VII] and [IX] can be obtained according to Process (1), (2) or (3) of this invention or by fermentation. The compounds of the general formula [X] can be obtained, for example, by a process comprising reacting a compound [XII] represented by the general formula [XII]:

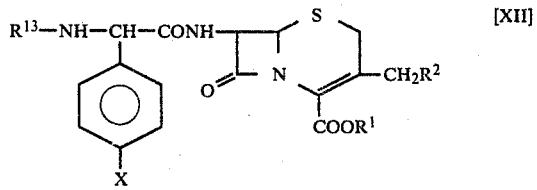

wherein X, $R^1$, $R^2$ and $R^{13}$ are as defined above, with the reactive derivative in the carboxyl group of a compound [III] explained hereinbefore.

This invention covers all the optical isomers and racemic compounds as well as all crystalline forms and hydrates of the compound of the general formula [I].

The embodiments of each of the production processes of the invention are described below.

In practising Process (1) or (2), a compound represented by formula [II] or [IV] is dissolved or suspended in a solvent inert to the reaction such as water, acetone, tetrahydrofuran, dioxane, acetonitrile, dimethylformamide, methanol, ethanol, propanol, butanol, 2-methoxyethanol, diethyl ether, isopropyl ether, benzene, toluene, methylene chloride, chloroform, ethyl acetate, methyl isobutyl ketone or the like alone or in admixture of two or more, and then reacted with a reactive derivative in the carboxyl group of the compound of formula [III] or with a compound of formula [V] or with a reactive derivative in the carboxyl group of the compound of formula [V] in the presence or absence of a base. In case a compound of formula [V] is used in the form of free acid or its salt as a reactant, the reaction is carried out usually in the presence of a dehydrating condensing agent. In this case, the reaction temperature is usually in the range of −40° C. to +50° C., preferably −20° C. to +20° C., and the reaction time usually ranges from 10 minutes to 10 hours. However, the conditions for the reaction are not restricted to those specified above and may be varied appropriately depending upon the kind of reactant. The bases usable in this reaction include inorganic bases such as alkali hydroxides, alkali hydrogen carbonates, alkali carbonates and alkali acetates; and organic nitrogen-containing bases such as trimethylamine, triethylamine, tributylamine, pyridine, N-methylpiperidine, N-methylmorpholine, lutidine, collidine, dimethylbenzylamine, dimethylaniline, diethylamine, dicyclohexylamine and the like.

Examples of said dehydrating condensing agent include N,N′-dicyclohexyl carbodiimide, N-cyclohexyl-N′-morpholinoethyl carbodiimide, N,N′-carbonyl di-(2-methylimidazole), dimethylchloroformiminium chloride, dimethylethoxyformiminium chloride, trialkyl phosphite, phosphorus oxychloride, phosphorus trichloride, thionyl chloride, oxalyl chloride and the like.

In practising Process (3), a compound represented by formula [VI] is reacted with an iminohalogenating agent in the first step (iminohalogenation reaction). The iminohalogenating agents most frequently used are, for example, phosphorus trichloride, phosphorus pentachloride, phosphorus tribromide, phosphorus pentabromide, phosphorus oxychloride, thionyl chloride, phosgene and the like. The reaction is usually carried out in a solvent. As the solvent there are most frequently used methylene chloride, chloroform, benzene, dichloroethane, trichloroethane, tetrachlorethane and the like, though other solvents inert to the reaction such as tetrahydrofuran, dioxane, dimethoxyethane may also be used. Although the temperature for the iminohalogenation reaction is not particularly limited, it is usually preferable to carry out the reaction under cooling. In the next step, the reaction product thus obtained is reacted with an iminoetherifying agent (iminoetherification reaction). The iminoetherifying agents usable in this step are, for example, alcohols such as methyl alcohol, ethyl alcohol, propyl alcohol, isopropyl alcohol, butyl alcohol, isobutyl alcohol, tert.-butyl alcohol, benzyl alcohol, methoxymethyl alcohol and the like; and alkali metal alkoxides thereof. Although the temperature for the iminoetherification reaction is not particularly limited, it is usual to carry out the reaction under cooling or at an elevated temperature.

In the next step, the reaction product thus obtained is reacted with a reactive derivative in the carboxyl group of the compound of formula [III] (acylation reaction). Although temperature of the acylation reaction is not particularly limited, it is usual to carry out the reaction under cooling or heating. In carrying out this step of the reaction, the liquid reaction mixture obtained in the preceding step may be used directly or after being concentrated under reduced pressure to distill off the excessive iminohalogenating agent and iminoetherifying agent. In the acylation reaction, there may be used as a solvent at least one member selected from water, acetone, dimethylformamide and the solvents used in the above-mentioned iminohalogenation and iminoetherification.

The above-mentioned iminohalogenation, iminoetherification and acylation may be carried out in the presence of an organic base such as dimethylaniline, pyridine, quinoline, picoline, lutidine, trialkylamine, dialkylbenzylamine or the like, according to a conventional method. The acylation product thus obtained is then hydrolyzed. The hydrolysis reaction proceeds sufficiently by pouring into water the liquid reaction mixture as obtained in the preceding step containing the reaction product. However, the mode of hydrolysis is not limited to the above but the conditions of hydrolysis may be varied appropriately depending upon the kind of reactant.

In practising Process (4), a compound represented by formula [VII] is reacted with a compound represented by formula [VIII] in a solvent inert to the reaction or a mixture of two or more of the solvents when $R^9$ in formula [VII] is other than the heterocyclic aromatic amine-N-oxide-thio group in which the thio group is attached to the carbon atom adjacent to the N-oxide group in the molecule. The solvent inert to the reaction includes, for example, water, methanol, ethanol, propanol, isopropanol, butanol, acetone, methyl ethyl ketone, methyl isobutyl ketone, tetrahydrofuran, dioxane, acetonitrile, ethyl acetate, 2-methoxyethanol, dimethoxyethane, dimethylformamide, dimethylsulfoxide, dichlorethane, chloroform, dichloromethane and the like.

Preferably, the reaction is carried out in a solvent of high polarity such as water. It is advantageous to keep the pH value of the reaction solution in the range of 2 to 10, particularly 4 to 8. The pH of the solution may be adjusted to the desired value by adding a buffer such as sodium phosphate. Though the reaction conditions are not particularly limited, the reaction is usually carried out at a temperature of 0° to 100° C. over a period of several hours to several tens of hours.

When $R^9$ in formula [VII] is a heterocyclic aromatic amine-N-oxide-thio group in which the thio group is attached to the carbon atom adjacent to the N-oxide group in the molecule, a compound represented by formula [VII] is reacted with a compound represented by formula [VIII] in the aforesaid inert solvent in the presence of a cupric compound. This reaction is particularly useful when the compound represented by formula [VIII] is an alcohol such as methyl alcohol, ethyl alcohol, propyl alcohol, isopropyl alcohol, n-butyl alcohol, benzyl alcohol, ethylene glycol or the like. In this case, the alcohol may be used in an excess to allow it to function as a solvent, too, whereby the reaction proceeds smoothly. The cupric compound used in this reaction include inorganic and organic cupric compounds such as cupric chloride, cupric bromide, cupric fluoride, cupric nitrate, cupric sulfate, cupric borate, cupric phosphate, cupric cyanide, cupric formate, cupric acetae, cupric propionate, cupric citrate, cupric tartrate, cupric benzoate, cupric salicylate and the like. Preferably said cupric compound is used in an amount of ½ mole or more per mole of the compound represented by the formula [VII].

Although the reaction temperature and reaction time may be varied depending upon the kinds of the compound of formula [VII], the cupric compound and the compound of formula [VIII], the reaction is generally effected at a temperature ranging from 0° C. to 100° C. for a period of time ranging from several minutes to several days.

However, the reaction conditions are not particularly limited to those specified above, and may appropriately be varied depending upon the kind of reactants.

In practising Process (5) of this invention, a compound represented by the general formula [IX] is subjected to conventional elimination reaction to eliminate the blocking group $R^8$. Concrete means for the elimination include catalytic reduction, chemical reduction, and other treatments under mild conditions such as hydrolysis, alcoholysis and the like. As is obvious from the description given above, the method for eliminating the blocking group may be varied depending upon the kind of blocking group. When $R^8$ is a benzhydryl group, a compound represented by the general formula [IX] is dissolved in anisole and reacted with trifluoroacetic acid to eliminate the benzhydryl group, which is a conventional method. When $R^8$ is a $\beta,\beta,\beta$-trichloroethyl group, a compound represented by the general formula [IX] is dissolved in a solvent such as dimethylformamide or the like and then reduced with powdered zinc to eliminate the $\beta,\beta,\beta$-trichlorethyl group. When $R^8$ is an organic silyl, organic phosphorus-containing or organic tin-containing group, it is usual that a mere treatment with water or an alcohol is enough to eliminate the blocking group with ease. In eliminating the blocking group by the above-mentioned methods, the reaction temperature and reaction time may be varied freely so as to obtain optimum conditions.

In practicing Process (6), a compound represented by the general formula [X] is dissolved or suspended in a solvent inert to the reaction such as tetrahydrofuran, dioxane, ethylene glycol dimethyl ether, methylene chloride, chloroform, dimethylformamide, dimethylacetamide, acetonitrile, methanol or the like alone or in admixture of two or more, and then reacted with the compound of the general formula [XI] in methanol. In this reaction, the methanol is used in an amount of one equivalent or more, and the amount of the compound [XI] is preferably 2 to 6 equivalents per equivalent of the compound [X].

To the resulting reaction solution is added a halogenating agent, and the resulting mixture is subjected to reaction. The halogenating agent is used in an amount enough to supply a positive halogen in an amount equivalent to the compound [X], and preferably used in an amount of 1 to 2 equivalents. When the halogenating agent is used in excess, the replacement of the hydrogen atoms on the phenyl nucleus of

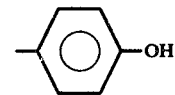

by the halogen atoms takes place simultaneously with said reaction.

All the reactions in Process (6) are generally effected at a temperature of $-120°$ to $-10°$ C., preferably $-100°$ to $-50°$ C., for a period of 5 to 30 minutes. The reaction is terminated by making the reaction system acidic.

The halogenating agent which may be used in Process (6) is one which is conventionally known as a positive-halogen-supplier, for example, any halide which can supply a positive halogen such as $Cl^+$, $Br^+$, $I^+$ or the like. Concrete examples thereof are halogens, such as chlorine, bromine or the like; N-haloimides, such as N-chlorosuccinimide, N-bromosuccinimide and the like; N-haloamides, such as N-bromoacetamide, N-chloroacetamide and the like; N-halosulfonamides, such as N-chlorobenzenesulfonamide, N-chloro-p-toluenesulfonamide and the like; 1-halobenztriazoles; 1-halotriazines; organic hypohalogenites such as tert.-butyl hypochlorite, tert.-butyl hypoiodite, and the like; halohydantoins such as N,N-dibromohydantoin and the like. Among them, tert.-butyl hypochlorite is preferred.

A suitable acid which may be used for terminating the reaction is such that when the acid is added under cooling there is caused neither solidification of the reaction mixture nor the freezing of the reaction mixture into a heavy, viscouse mixture, and there may be used, for example, 98% formic acid, glacial acetic acid, trichloroacetic acid, methane sulfonic acid and the like.

After the termination of the reaction, the excessive halogenating agent is removed by treating the reaction product with a reducing agent, such as sodium thiosulfate or the like, or a trialkyl ester of phosphoruous acid, such as trimethyl phosphite, triethyl phosphite, tributyl phosphite or the like.

The reaction conditions are not particularly limited to those specified above, and may appropriately be varied depending upon the kind of reactants.

The 7α-methoxy-cephalosporins of the general formula [I] produced according to one of the above-mentioned processes can be isolated and collected by a conventional method. The compounds of the general formula [I] in which $R^1$ represents a non-toxic salt-forming cation can also be obtained by a conventional method from those compounds of the general formula [I] in which $R^1$ represents a hydrogen atom or a blocking group.

The compound of the general formula [I] of this invention not only has a broad antibacterial spectrum against Gram-positive and Gram-negative bacteria but also exhibits a quite excellent antibacterial activity against *Pseudomonas aeruginosa*, is resistant to the action of cephalosporinase, and therefore is quite valuable as a therapeutic medicine for human and animal diseases.

Concrete examples of the 7α-methoxycephalosprins of this invention are listed in Table 1 in which combinations of the groups A, X, $R^1$, $R^2$, $R^3$ and $R^4$ in the general formula [I] are shown.

Table 1

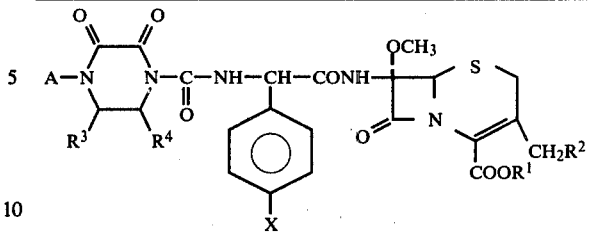

| A | X | $R^1$ | $R^2$ | $R^3$ | $R^4$ |
|---|---|---|---|---|---|
| CH₃ | H | H | H | H | H |
| " | OH | " | " | " | " |
| C₂H₅ | H | " | " | " | " |
| " | " | " | " | " | CH₃ |
| " | " | " | " | CH₃ | H |
| " | OH | " | " | H | " |
| " | " | " | " | " | CH₃ |
| " | " | " | " | CH₃ | H |
| iso-C₃H₇ | H | " | " | H | " |
| " | OH | " | " | " | " |
| n-C₃H₇ | H | " | " | " | " |
| " | OH | " | " | " | " |
| n-C₄H₉ | H | " | " | " | " |
| " | OH | " | " | " | " |
| n-C₈H₁₇ | H | " | " | " | " |
| " | OH | " | " | " | " |
| CH₃ | H | " | —OCOCH₃ | " | " |
| " | OH | " | " | " | " |
| " | " | " | " | " | CH₃ |
| C₂H₅ | H | " | " | H | " |
| " | " | " | " | " | CH₃ |
| " | " | " | " | CH₃ | H |
| " | OH | " | " | H | " |
| " | " | " | " | " | CH₃ |
| " | " | " | " | CH₃ | H |
| iso-C₃H₇ | H | " | " | H | " |
| " | OH | " | " | " | " |
| n-C₃H₇ | H | " | " | " | " |
| " | OH | " | " | " | " |
| n-C₄H₉ | H | " | " | " | " |

Table 1-continued

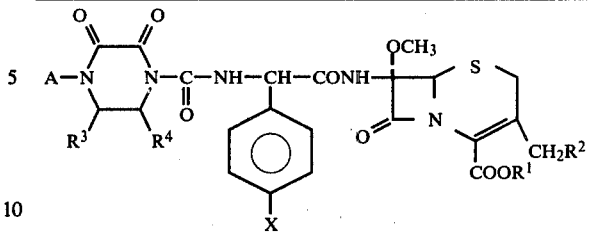

| A | X | $R^1$ | $R^2$ | $R^3$ | $R^4$ |
|---|---|---|---|---|---|
| " | OH | " | " | " | " |
| n-C₈H₁₇ | H | " | " | " | " |
| " | OH | " | " | " | " |
| ClCH₂CH₂ | H | " | " | " | " |
| " | OH | " | " | " | " |
| HOCH₂CH₂ | H | " | " | " | " |
| " | OH | " | " | " | " |
| CH₃ | H | " | —OCONH₂ | " | " |
| " | OH | " | " | " | " |
| C₂H₅ | H | " | " | " | " |
| " | " | " | " | " | CH₃ |
| " | " | " | " | CH₃ | " |
| " | OH | " | " | H | H |
| " | " | " | " | " | CH₃ |
| " | " | " | " | CH₃ | H |
| iso-C₃H₇ | H | " | " | H | " |
| " | OH | " | " | " | " |
| n-C₃H₇ | H | " | " | " | " |
| " | OH | " | " | " | " |
| n-C₄H₉ | H | " | " | " | " |
| " | OH | " | " | " | " |
| n-C₈H₁₇ | H | " | " | " | " |
| " | OH | " | " | " | " |
| CH₃ | H | " | 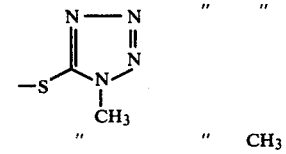 | " | " |
| " | " | " | " | " | CH₃ |
| " | " | " | " | CH₃ | H |
| " | OH | " | " | H | " |
| " | " | " | " | " | CH₃ |
| " | " | " | " | CH₃ | H |
| C₂H₅ | H | " | " | H | " |
| " | " | " | " | " | CH₃ |
| " | " | " | " | CH₃ | H |
| " | OH | " | " | H | " |
| " | " | " | " | " | CH₃ |
| " | " | " | " | CH₃ | H |
| iso-C₃H₇ | H | " | " | H | " |
| " | OH | " | " | " | " |
| n-C₃H₇ | H | " | " | " | " |
| " | OH | " | " | " | " |
| n-C₄H₉ | H | " | " | " | " |
| " | OH | " | " | " | " |
| n-C₆H₁₃ | H | " | " | " | " |
| " | OH | " | " | " | " |
| n-C₈H₁₇ | H | " | " | " | " |
| " | OH | " | " | " | " |
| CH₃ | H | " | 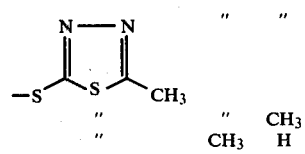 | " | " |
| " | " | " | " | " | CH₃ |
| " | " | " | " | CH₃ | H |
| " | OH | " | " | H | " |
| " | " | " | " | " | CH₃ |
| " | " | " | " | CH₃ | H |
| C₂H₅ | H | " | " | H | " |
| " | " | " | " | " | CH₃ |
| " | " | " | " | CH₃ | H |
| " | OH | " | " | H | " |
| " | " | " | " | " | CH₃ |
| " | " | " | " | CH₃ | H |
| iso-C₃H₇ | H | " | " | H | " |
| " | OH | " | " | " | " |
| n-C₃H₇ | H | " | " | " | " |

Table 1-continued

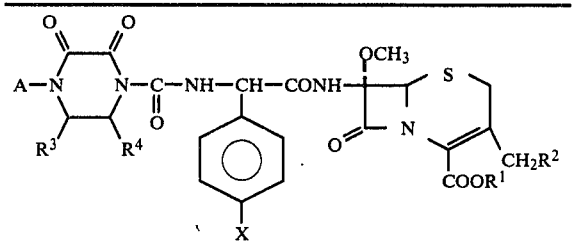

| A | X | R¹ | R² | R³ | R⁴ |
|---|---|---|---|---|---|
| " | OH | " | " | " | " |
| n-C₄H₉ | H | " | " | " | " |
| " | OH | " | " | " | " |
| n-C₆H₁₃ | H | " | " | " | " |
| " | OH | " | " | " | " |
| n-C₈H₁₇ | H | " | " | " | " |
| " | OH | " | " | " | " |
| CH₃ | H | " | -S-[1,3,4-thiadiazole] | " | " |
| " | OH | " | " | " | " |
| C₂H₅ | H | " | " | " | " |
| " | OH | " | " | " | " |
| iso-C₃H₇ | H | " | " | " | " |
| " | OH | " | " | " | " |
| n-C₃H₇ | H | " | " | " | " |
| " | OH | " | " | " | " |
| n-C₄H₉ | H | " | " | " | " |
| " | OH | " | " | " | " |
| CH₃ | H | " | —OCH₃ | " | " |
| " | OH | " | " | " | " |
| C₂H₅ | H | " | " | " | " |
| " | OH | " | " | " | " |
| iso-C₃H₇ | H | " | " | " | " |
| " | OH | " | " | " | " |
| n-C₃H₇ | H | " | " | " | " |
| " | OH | " | " | " | " |
| n-C₄H₉ | H | " | " | " | " |
| " | OH | " | " | " | " |
| CH₃ | H | " | -S-[1,2,4-triazole-H] | " | " |
| " | OH | " | " | " | " |
| C₂H₅ | H | " | " | " | " |
| " | OH | " | " | " | " |
| n-C₃H₇ | H | " | " | " | " |
| " | OH | " | " | " | " |
| n-C₄H₉ | H | " | " | " | " |
| " | OH | " | " | " | " |
| CH₃ | H | " | -S-[1,2,4-triazole-CH₃] | " | " |
| " | OH | " | " | " | " |
| C₂H₅ | H | " | " | " | " |
| " | OH | " | " | " | " |
| n-C₃H₇ | H | " | " | " | " |
| " | OH | " | " | " | " |
| n-C₄H₉ | H | " | " | " | " |
| " | OH | " | " | " | " |
| CH₃ | H | " | -S-[1,2,3-triazole-H] | " | " |
| " | OH | " | " | " | " |
| C₂H₅ | H | " | " | " | " |
| " | OH | " | " | " | " |
| n-C₃H₇ | H | " | " | " | " |
| " | OH | " | " | " | " |
| n-C₄H₉ | H | " | " | " | " |
| " | OH | " | " | " | " |

Table 1-continued

| A | X | R¹ | R² | R³ | R⁴ |
|---|---|---|---|---|---|
| CH₃ | H | " | -S-[tetrazole-H] | " | " |
| " | OH | " | " | " | " |
| C₂H₅ | H | " | " | " | " |
| " | OH | " | " | " | " |
| n-C₃H₇ | H | " | " | " | " |
| " | OH | " | " | " | " |
| n-C₄H₉ | H | " | " | " | " |
| " | OH | " | " | " | " |
| CH₃ | H | " | -S-[1,3,4-oxadiazole-CH₃] | " | " |
| " | OH | " | " | " | " |
| C₂H₅ | H | " | " | " | " |
| " | OH | " | " | " | " |
| n-C₃H₇ | H | " | " | " | " |
| " | OH | " | " | " | " |
| n-C₄H₉ | H | " | " | " | " |
| " | OH | " | " | " | " |
| CH₃ | H | " | -S-[thiazole-CH₃] | " | " |
| " | OH | " | " | " | " |
| C₂H₅ | H | " | " | " | " |
| " | OH | " | " | " | " |
| CH₃ | H | " | -S-[pyridine-N-oxide] | " | " |
| " | OH | " | " | " | " |
| C₂H₅ | H | " | " | " | " |
| " | OH | " | " | " | " |
| n-C₃H₇ | H | " | " | " | " |
| " | OH | " | " | " | " |
| n-C₄H₉ | H | " | " | " | " |
| " | OH | " | " | " | " |
| CH₃ | H | " | -S-[tetrazole-C₂H₅] | " | " |
| " | OH | " | " | " | " |
| C₂H₅ | H | " | " | " | " |
| " | OH | " | " | " | " |
| " | H | " | -S-[triazinone-CH₃,N-CH₃] | " | " |
| " | OH | " | " | " | " |

Table 1-continued

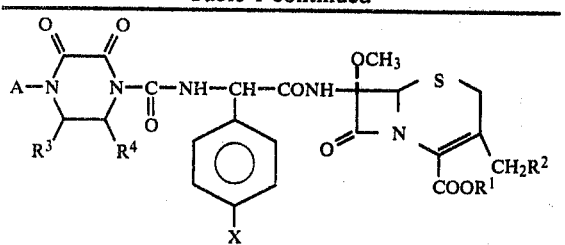
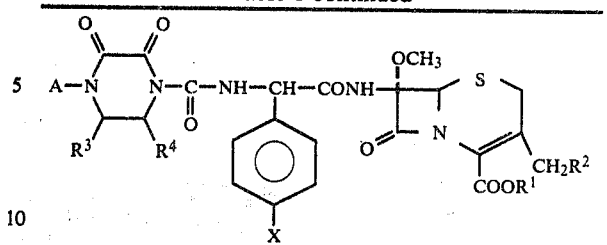

| A | X | R¹ | R² | R³ | R⁴ |
|---|---|---|---|---|---|
| " | H | " | (structure: -S-C(=N-CH₃)-O- ring with CH₃) | " | " |
| " | OH | " | " | " | " |
| " | H | " | (structure: -S-C(=N)-S- thiazole ring) | " | " |
| " | OH | " | " | " | " |
| " | H | " | (structure: -S-C(=N)-N(CH₃)- ring) | " | " |
| " | OH | " | " | " | " |
| " | H | " | (structure: -S-pyridazine-CH₃, N=N) | " | " |
| " | OH | " | " | " | " |
| " | H | " | (structure: -S-pyrimidine N,N) | " | " |
| " | OH | " | " | " | " |
| " | H | " | —SCH₃ | " | " |
| " | OH | " | " | " | " |
| " | H | " | —OCH₃ | " | " |
| " | OH | " | " | " | " |
| " | H | " | —SCH₂CH₂CH₃ | " | " |
| " | OH | " | " | " | " |
| " | H | " | —SCH₂CH₃ | " | " |
| " | OH | " | " | " | " |
| " | H | " | —S(CH₂)₃CH₃ | " | " |
| " | OH | " | " | " | " |
| " | H | " | —SCH₂COOCH₂CH₃ | " | " |
| " | OH | " | " | " | " |
| " | H | " | —SCH₂COOH | " | " |
| " | OH | " | " | " | " |

The compounds of the general formula [I] also include non-toxic salts, such as sodium salt, of the compounds having the groups shown in Table 1, and those compounds in which the carboxyl group is blocked by a blocking group such as $\beta,\beta,\beta$-trichloethyl ester group.

The compounds of the general formula [I] of this invention are administered to human and animals in the form of a free acid, a non-toxic salt or a physiologically acceptable ester. Said compounds are formed into preparations usually adopted in penicillin or cephalosporin medicines, such as tablets, capsules, syrups or injections, and then administered orally or parenterally.

The susceptible test of typical compounds among the compounds of the present invention is shown below.

The minimum inhibitory concentrations (MIC) of the compounds against different strains are shown in Table 2.

The minimum inhibitory concentration (MIC) was determined by the plate method disclosed in "Chemotherapy" (Japan), Vol. 16, (1968), pages 98–99. The culture medium used was a Heart Infusion agar (pH 7.4). The number of the cells per plate used in the inoculum was $10^4$ ($10^6$ cells/ml).

Table 2

| Name of bacterium | Compound No. | | | | |
|---|---|---|---|---|---|
| | 1 | 2 | 3 | 4 | 5 |
| *Staphylococcus aureus* F-19 (Penicillinase-producing bacterium) | 6.25 | 6.25 | 12.5 | 12.5 | 25 |
| *Escherichia coli* NIHJ | ≦0.1 | ≦0.1 | ≦0.1 | ≦0.1 | ≦0.1 |
| *Klebsiella pneumoniae* Y-50 | 0.78 | 0.2 | 1.56 | 1.56 | 0.78 |
| *Proteus vulgaris* GN 76 (Cephalosporinase-producing bacterium) | 0.78 | 0.39 | 3.13 | 1.56 | 3.13 |
| *Pseudomonas aeruginosa* IFO-3445 | 12.5 | 6.25 | 100 | 50 | 12.5 |
| *Serratia marcescens* W-8 | 50 | 100 | 200 | 200 | 200 |
| *Citrobacter spp* Toyama Citizen No. 31 | 1.56 | 1.56 | 6.25 | — | — |
| *Acinetobacter calcoaceticus* A-6 | 12.5 | 6.25 | 25 | — | — |
| *Citrobacter freundii* GN 346 (Cephalosporinase-producing bacterium) | 100 | 100 | >200 | — | 25 |
| *Enterobacter cloacae* | 25 | 100 | 100 | 100 | 100 |

Table 2-continued

| Name of bacterium | Compound No. | | | | |
|---|---|---|---|---|---|
| | 1 | 2 | 3 | 4 | 5 |
| IID 977 | | | | | |

Note:
The structural formulas and chemical names of Compound Nos. 1 to 5 in Table 2 are as follows:

Compound No. 1

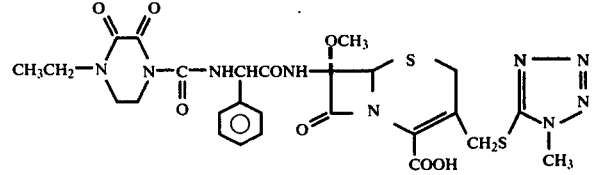

7β-[D(-)-α-(4-ethyl-2,3-dioxo-1-piperazinylcarbonylamino)-phenylacetamido]-7α-methoxy-3-[5-(1-methyl-1,2,3,4-tetrazolyl)thiomethyl]-Δ³-cephem-4-carboxylic acid.

Compound No. 2

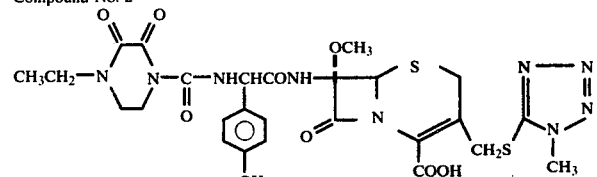

7β-[D(-)-α-(4-ethyl-2,3-dioxo-1-piperazinylcarbonylamino)-p-hydroxyphenylacetamido]-7α-methoxy-3-[5-(1-methyl-1,2,3,4-tetrazolyl)thiomethyl]-Δ³-cephem-4-carboxylic acid.

Compound No. 3

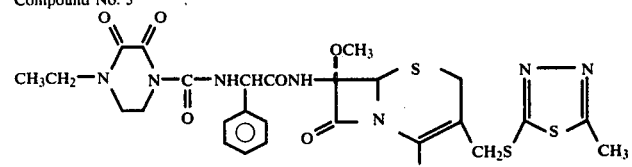

7β-[D(-)-α-(4-ethyl-2,3-dioxo-1-piperazinylcarbonylamino)-phenylacetamino]-7α-methoxy-3-[2-(5-methyl-1,3,4-thiadiazolyl)thiomethyl]-Δ³-cephem-4-carboxylic acid.

Compound No. 4

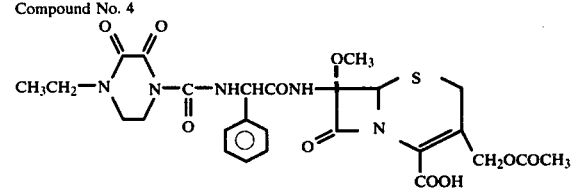

7β-[D(-)-α-(4-ethyl-2,3-dioxo-1-piperazinylcarbonylamino)-phenylacetamido]-7α-methoxy-3-acetoxymethyl-Δ³-cephem-4-carboxylic acid.

Compound No. 5

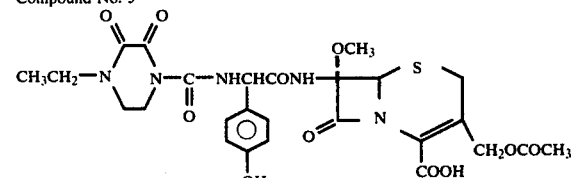

7β-[D(-)-α-(4-ethyl-2,3-dioxo-1-piperazinylcarbonylamino)-p-hydroxyphenylacetamido]-7α-methoxy-3-acetoxymethyl-Δ³-cephem-4-carboxylic acid.

Referring to Examples, this invention will be further explained in detail below. The Examples are by way of illustration and not by way of limitation.

EXAMPLE 1

(1) In 15 ml of anhydrous methylene chloride was suspended 0.62 g of D(—)-α-(4-ethyl-2,3-dioxo-1-piperazinylcarbonylamino)phenylacetic acid, and 0.2 g of N-methylmorpholine was then added thereto to form a solution. The resulting solution was cooled to —20° C., to which 5 ml of a solution of 0.21 g of ethyl chlorocarbonate in anhydrous methylene chloride was then added, and the resulting mixture was reacted for 60 minutes at a temperature of —10° C. to 0° C. A solution of 0.94 g of benzhydryl 7β-amino-3-acetoxymethyl-7α-methoxy-Δ³-cephem-4-carboxylate in 5 ml of anhydrous methylene chloride was then dropped into the mixture. The resulting mixture was reacted at a temperature of —20° to 0° C. for 30 minutes, then at a temperature of 0° to 10° C. for 60 minutes and further at room temperature for 60 minutes, after which the reaction liquid was concentrated to dryness under reduced pressure. The residue was dissolved in a mixture of 25 ml of water and 25 ml of ethyl acetate and the pH value thereof was adjusted to 1.5 by adding 2 N hydrochloric acid with ice-cooling. The ethyl acetate layer was separated off, washed successively with 5% aqueous solution of sodium hydrogen carbonate and saturated aqueous solution of sodium chloride, and dried over anhydrous magnesium sulfate, after which the solvent was distilled off under reduced pressure. The residue was purified by means of column chromatography on silica gel, where the eluant was a 1:1 (by volume) mixture of ethyl acetate and benzene. Thus, there was obtained, in a crystalline form, 0.94 g (yield 61.1%) of benzhydryl 7β-[D(−)-α-(4-ethyl-2,3-dioxo-1-piperazinylcarbonylamino)phenylacetamido]-7α-methoxy-3-acetoxymethyl-Δ³-cephem-4-carboxylate melting at 106° to 109° C. with decomposition.

IR (KBr) cm$^{-1}$: $\nu_{N-H}$ 3275, $\nu_{C=O}$ 1770, 1730–1670

NMR (CDCl$_3$), ppm values: 1.15 (CH$_3$, 3H), 1.9 (CH$_3$, 3H), 3.4 (CH$_3$, 3H), 3.3–3.5 (CH$_2$×3, 6H), 3.95 (CH$_2$, 2H), 4.5 (CH$_2$, 2H), 5.25 (CH, 1H), 5.65 (CH, 1H), 6.84 (CH, 1H), 7.3 (C$_6$H$_5$×3, 15H), 8.0 (NH, 1H), 9.9 (NH, 1H)

(2) In 20 ml of anisole was dissolved 0.77 g of benzhydryl 7β-[D(−)-α-(4-ethyl-2,3-dioxo-1-piperazinylcarbonylamino)phenylacetamido]-7α-methoxy-3-acetoxymethyl-Δ³-cephem-4-carboxylate obtained in above (1), to which 8 ml of trifluoroacetic acid was added with ice-cooling. The resulting mixture was stirred at room temperature for 30 minutes, after which the excessive trifluoroacetic acid and anisole were distilled off under reduced pressure. The residue was dissolved in a mixture composed of 25 ml of ethyl acetate and 25 ml of water and the pH value thereof was adjusted to 7.0 with sodium hydrogen carbonate. The aqueous layer was separated, 25 ml of fresh ethyl acetate was added thereto, and the pH value of the mixture was adjusted to 1.5 by adding 2 N hydrochloric acid with cooling. The ethyl acetate layer was separated, thoroughly washed with water, and dried over anhydrous magnesium sulfate, after which the solvent was distilled off under reduced pressure. Thus, there was obtained, in a crystalline form, 0.52 g (yield 86.2%) of 7β-[D-(−)-α-(4-ethyl-2,3-dioxo-1-piperazinylcarbonlamino)-phenylacetamido]-7α-methoxy-3-acetoxymethyl-Δ³-cephem-4-carboxylic acid melting at 135° to 140° C. with decomposition.

IR (KBr) cm$^{-1}$: $\nu_{C=O}$ 1771, 1730–1670

NMR(CDCl$_3$) ppm values:

1.15 (CH$_3$, 3H), 2.0 (CH$_3$, 3H), 3.4 (CH$_3$, 3H), 3.3–3.6 (CH$_2$×3, 6H), 4.0 (CH$_2$, 2H), 4.5–5.0 (CH$_2$, 2H), 5.0 (CH, 1H), 5.5 (CH, 1H), 7.3 (C$_6$H$_5$, 5H), 8.3 (NH, 1H), 9.95 (NH, 1H)

The resistant activity against β-lactamase of the product obtained above was as shown in Table 3 in which comparisons are shown:

Table 3

| Compound | Cephalosporinase* | | Penicillinase** E. coli TK-3 |
|---|---|---|---|
| | Pseudomonas aeruginosa TN 918 | Serratia W-8 | |
| Potassium Penicillin G | 16 | 21 | 100 |
| Cephalorigine | 100 | 100 | 115 |
| Product obtained above | <0.4 | <0.06 | <0.04 |

Note:
*Each numeral shown in Table 3 is a relative activity value calculated by assuming as 100 the activity of the control Cephalorigine.
**Each numeral shown in Table 3 is a relative activity value calculated by assuming as 100 the activity of the control potassium Penicillin G.

The resistance of each compound against β-lactamase was determined by the iodometric assay method.

The following compounds were obtained in the same manner as above:

7β-[D(−)-α-(4-methyl-2,3-dioxo-1-piperazinylcarbonylamino)phenylacetamido]-7α-methoxy-3-acetoxymethyl-Δ³-cephem-4-carboxylic acid Melting point: 133°–138° C. (decomposed)
IR (KBr) cm$^{-1}$: $\nu_{C=O}$ 1772, 1730–1670

7β-[D(−)-α-(4-n-butyl-2,3-dioxo-1-piperazinylcarbonylamino)phenylacetamido]-7α-methoxy-3-acetoxymethyl-Δ³-cephem-4-carboxylic acid Melting point: 130°–131° C. (decomposed)
IR (KBr) cm$^{-1}$: $\nu_{C=O}$ 1775, 1730–1670

7β-[D(−)-α-(4-ethyl-2,3-dioxo-1-piperazinylcarbonylamino)-p-hydroxyphenylacetamido]-7α-methoxy-3-acetoxymethyl-Δ³-cephem-4-carboxylic acid Melting point: 146°–150° C. (decomposed)
IR (KBr) cm$^{-1}$: $\nu_{C=O}$ 1771, 1730–1670

The above-obtained product was adjusted to a pH of 7.0 by neutralization with an aqueous sodium hydrogen carbonate solution, and then subjected to filtration and lyophilization to obtain a sodium salt thereof.

7β-[D(−)-α-(4-ethyl-2,3-dioxo-1-piperazinylcarbonylamino)phenylacetamido]-7α-methoxy-3-carbamoyloxymethyl-Δ³-cephem-4-carboxylic acid Melting point: 165°–170° C. (decomposed)
IR (KBr) cm$^{-1}$: $\nu_{C=O}$ 1775, 1720–1680

7β-[D(−)-α-(4-ethyl-2,3-dioxo-1-piperazinylcarbonylamino)-p-hydroxyphenylacetamido]-7α-methoxy-3-carbamoyloxymethyl-Δ³-cephem-4-carboxylic acid Melting point: 177°–181° C. (decomposed)
IR (KBr) cm$^{-1}$: $\nu_{C=O}$ 1775, 1730–1680

EXAMPLE 2

(1) In 10 ml of anhydrous methylene chloride was dissolved 0.78 g of benzhydryl 7β-amino-7α-methoxy-3-[5-(1-methyl-1,2,3,4-tetrazolyl)thiomethyl]-Δ³-cephem-4-carboxylate and 0.73 g of N,N-dimethylaniline. A solution of 1.7 g of D(−)-α-(4-ethyl-2,3-dioxo-1-piperazinylcarbonylamino)phenylacetic acid chloride in anhydrous methylene chloride was added thereto with ice-cooling, and reaction was effected at a temperature of 0° to 10° C. for 30 minutes and then at room temperature for 3 hours. The reaction liquid was washed successively with 2 N hydrochloric acid, 5% aqueous solution of sodium hydrogen carbonate and water. The organic layer was separated off and dried over anhydrous magnesium sulfate, after which the solvent was distilled off under reduced pressure. Thus, there was obtained an oily product, which was then purified by means of column chromatography on silica gel with a 1:1 (by volume) mixture of ethyl acetate and benzene as eluant. Thus there was obtained, in a crystalline form, 0.88 g (yield 72.8%) of benzhydryl 7β-[(−)-α-(4-ethyl-2,3-dioxo-1-piperazinylcarbonylamino)phenylacetamido]-7α-methoxy-3-[5-(1-methyl-1,2,3,4-tetrazolyl)thiomethyl]-Δ³-cephem-4-carboxylate melting at 110°–118° C. with decomposition.

IR (KBr) cm$^{-1}$: $\nu_{N-H}$ 3280; $\nu_{C=O}$ 1775, 1705–1680

(NMR (CDCl$_3$) ppm values: 1.1 (CH$_3$, 3H), 3.4 (CH$_3$, 3H), 3.75 (CH$_3$, 3H), 3.2–3.8 (CH$_2$×3, 6H), 3.8–4.3 (CH$_2$×2, 4H), 5.0 (CH, 1H), 5.6 (CH, 1H), 6.72 (CH, 1H), 7.3 (C$_6$H$_5$×3, 15H), 9.85 (NH, 1H)

In 30 ml of anisole was dissolved 0.825 g of benzhydryl 7β-[D(−)-α-(4-ethyl-2,3-dioxo-1-piperazinylcarbonylamino)phenylacetamido]-7α-methoxy-3[5-(1-methyl-1,2,3,4-tetrazolyl)thiomethyl]-Δ³-cephem-4-carboxylate obtained in above (1). While cooling it with ice, 8 ml of trifluoroacetic acid was added thereto and reaction was effected at a temperature of 0° to 5° C. for one hour. The reaction liquid was concentrated to dryness under reduced pressure at a temperature below 35° C. The residue was dissolved in 30 ml of 2% aqueous solution of sodium hydrogen carbonate and washed twice with 10 ml portions of ethyl acetate. The water layer was separated off, mixed with 30 ml of fresh ethyl acetate, and adjusted to a pH value of 1.5 with 2 N hydrochloric acid. The ethyl acetate layer was separated off, thoroughly washed with saturated aqueous solution of sodium chloride and dried over anhydrous magnesium sulfate, after which the solvent was distilled off under reduced pressure. Thus there was obtained, in a crystalline form, 0.575 g (yield 87.2%) of 7β-[D(−)-α-(4-ethyl-2,3-dioxo-1-piperazinylcarbonylamino)-phenylacetamido]-7α-methoxy-3-[5-(1-methyl-1,2,3,4-tetrazolyl)thiomethyl]-Δ$^3$-cephem-4-carboxylic acid melting at 160°–165° C. with decomposition.

IR (KBr) cm$^{-1}$: $\nu_{N-H}$ 3280; $\nu_{C=O}$ 1750, 1710–1670

NMR (d$_6$-DMSO) ppm values: 1.1 (CH$_3$, 3H), 3.05 (CH$_2$, 2H), 3.41 (CH$_3$, 3H), 3.90 (CH$_3$, 3H), 3.2–4.0 (CH$_2$×3, 6H), 4.25 (CH$_2$, 2H), 5.08 (CH, 1H), 5.60 (CH, 1H), 5.2–5.8 (COOH, 1H), 7.38 (C$_6$H$_5$, 5H), 9.70 (NH, 1H), 9.95 (NH, 1H)

The following compounds were obtained in the same manner as above:

7β-[D(−)-α-(4-ethyl-2,3-dioxo-1-piperazinylcarbonylamino)-p-hydroxyphenylacetamido]-7α-methoxy-3-[5-(1-methyl-1,2,3,4-tetrazolyl)thiomethyl]-Δ$^3$-cephem-4-carboxylic acid Melting point: 173°–176° C. (decomposed)
IR (KBr) cm$^{-1}$: $\nu_{C=O}$ 1750, 1720–1678

2.6 Grams of the above-obtained compound was dissolved in a mixed solvent consisting of 20 ml of acetone and 5 ml of n-butyl alcohol, and 15 ml of n-butyl alcohol solution of 0.64 g of sodium 2-ethylhexanoate was added to this solution. The mixture was stirred for 1 hour to deposit crystals, which were then filtered off, washed with acetone, and dried to obtain 2.3 g of a sodium salt of 7β-[D(−)-α-(4-ethyl-2,3-dioxo-1-piperazinylcarbonylamino)-p-hydroxyphenylacetamido]-7α-methoxy-3-[5-(1-methyl-1,2,3,4-tetrazolyl)thiomethyl]-Δ$^3$-cephem-4-carboxylic acid, yield 84%.

7β-[D(−)-α-(4-ethyl-2,3-dioxo-1-piperazinylcarbonylamino)phenylacetamido]-7α-methoxy-3-[2-(5-methyl-1,3,4-thiadiazolyl)thiomethyl]-Δ$^3$-cephem-4-carboxylic acid Melting point: 169°–172° C. (decomposed)
IR (KBr) cm$^{-1}$: $\nu_{C=O}$ 1760, 1728–1670

7β-[D(−)-α-(4-ethyl-2,3-dioxo-1-piperazinylcarbonylamino)-p-hydroxyphenylacetamido]-7α-methoxy-3-[2-(5-methyl-1,3,4-thiadiazolyl)thiomethyl]-Δ$^3$-cephem-4-carboxylic acid Melting point: 179°–183° C. (decomposed)
IR (KBr) cm$^{-1}$: $\nu_{C=O}$ 1757, 1730–1670

EXAMPLE 3

(1) In 10 ml of anhydrous methylene chloride was suspended 0.32 g of D(−)-α-(4-ethyl-2,3-dioxo-1-piperazinylcarbonylamino)phenylacetic acid, and 0.1 g of N-methylmorpholine was then added thereto to form a solution. The solution was then cooled to −20° C., a solution of 0.11 g of ethyl chlorocarbonate in 3 ml of anhydrous methylene chloride was added thereto, and the resulting mixture was reacted for 60 minutes at a temperature of −10° to −5° C. Into the mixture was then dropped a solution of 0.37 g of β,β,β-trichlorethyl 7β-amino-3-methyl-7α-metoxy-Δ$^3$-cephem-4-carboxylate in 5 ml of anhydrous methylene chloride and reaction was effected at a temperature of −20° to 0° C. for 30 minutes, then at 0° to 10° C. for 60 minutes and further at room temperature for 60 minutes. The reaction liquid was concentrated to dryness under reduced pressure. The residue was dissolved in a mixture composed of 15 ml of ethyl acetate and 10 ml of water, and the pH of the resulting solution was adjusted to 1.5 with 2 N hydrochloric acid with ice-cooling. The ethyl acetate layer was separated off, washed successively with 5% aqueous solution of sodium hydrogen carbonate and saturated aqueous solution of sodium chloride and dried over anhydrous magnesium sulfate, after which the solvent was distilled off under reduced pressure and the residue was purified by means of column chromatography on silica gel with a 1:1 (by volume) mixture of ethyl acetate and benzene as eluant. Thus there was obtained, in a crystalline form, 0.45 g (yield 66.5%) of β,β,β-trichlorethyl 7β-[D(−)-α-(4-ethyl-2,3-dioxo-1-piperazinylcarbonylamino)phenylacetamido]-7α-methoxy-3-methyl-Δ$^3$-cephem-4-carboxylate melting at 120°–125° C. with decomposition.

IR (KBr) cm$^{-1}$: $\nu_{N-H}$ 3300; $\nu_{C=O}$ 1770, 1720–1670

NMR (d$_6$-DMSO) ppm values: 1.1 (CH$_3$, 3H), 2.0 (CH$_3$, 3H), 3.0–3.7 (CH$_2$×3, 6H), 3.40 (CH$_3$, 3H), 3.70–4.0 (CH$_2$, 2H), 4.90 (CH$_2$, 2H), 5.0 (CH, 1H), 5.65 (CH, 1H), 7.40 (C$_6$H$_5$, 5H), 9.55 (NH, 1H), 9.90 (NH, 1H)

(2) In 10 ml of N,N-dimethylformamide was dissolved 0.68 g of the β,β,β-trichlorethyl 7β-[D(−)-α-(4-ethyl-2,3-dioxo-1-piperazinylcarbonylamino)-phenylacetamido]-7α-methoxy-3-methyl-Δ$^3$-cephem-4-carboxylate obtained in above (1), to which 0.65 g of powdered metallic zinc and 5 drops of acetic acid were then added. The resulting mixture was reacted at room temperature for 1.5 hours. The reaction liquid was filtered off with diatomaceous earth, and the solvent was distilled off under reduced pressure. The residue was dissolved in a mixture of 20 ml of ethyl acetate and 10 ml of water. The pH value of the resulting solution mixture was adjusted to 1.5 with 2 N hydrochloric acid with ice-cooling. The ethyl acetate layer was separated and extracted twice with 10 ml portions of 5% aqueous solution of sodium hydrogen carbonate. The extracts were combined together, and mixed with 30 ml of fresh ethyl acetate. The pH of the mixture was adjusted to 1.5 with 2 N hydrochloric acid. The ethyl acetate layer was separated off, thoroughly washed with saturated aqueous solution of sodium chloride, and dried over anhydrous magnesium sulfate, after which the solvent was distilled off under reduced pressure. Thus there was obtained, in a crystalline form, 0.40 g (yield 77.7%) of 7β-[D(−)-α-(4-ethyl-2,3-dioxo-1-piperazinylcarbonylamino)-phenylacetamido]-7β-methoxy-3-methyl-Δ$^3$-cephem-4-carboxylic acid melting at 160°–163° C. with decomposition.

IR (KBr) cm$^{-1}$: $\nu_{N-H}$ 3280; $\nu_{C=O}$ 1760, 1720–1665

NMR (d$_6$-DMSO) ppm values: 1.1 (CH$_3$, 3H), 2.0 (CH$_3$, 3H), 3.0–3.7 (CH$_2$ x 3, 6H), 3.4 (CH$_3$, 3H), 3.7–4.1 (CH$_2$, 2H), 5.0 (CH, 1H), 5.65 (CH, 1H), 7.40 (C$_6$H$_5$, 5H), 9.70 (NH, 1H), 9.90 (NH, 1H)

EXAMPLE 4

In 8 ml of anhydrous chloroform was dissolved 0.60 g of benzhydryl 7β-D(−)-α-aminophenylacetamido-7α-methoxy-3-acetoxymethyl-Δ$^3$-cephem-4-carboxylate, to which was added 0.10 g of N-methylmorpholine. To the solution cooled to 0° C. was added 0.21 g of 4-ethyl-2,3-dioxo-1-piperazinylcarbonyl chloride, and after which the temperature of the solution was elevated to room temperature, at which the solution was reacted for 2 hours. The reaction liquid was concentrated to dryness under reduced pressure, and the residue was dissolved in a mixture of 20 ml of water and 20 ml of ethyl acetate. The ethyl acetate layer was separated and mixed with 20 ml of water. The pH value of the mixture was adjusted to 7.2 with sodium hydrogen carbonate. The ethyl acetate layer was separated off, thoroughly washed with water and dried over anhydrous magnesium sulfate, after which the solvent was distilled off under reduced pressure. The residue was purified by means of column chromatography on silica gel with a 1:1 (by volume) mixture of ethyl acetate and benzene as eluant. Thus there was obtained, in a crystalline form, 0.5 g (yield 65%) of benzhydryl 7β-[D(−)-α-(4-ethyl-2,3-dioxo-1-piperazinylcarbonylamino)-phenylacetamido]-7α-methoxy-3-acetoxymethyl-Δ³-cephem-4-carboxylate melting at 106°–109° C. with decomposition. This product had the same IR and NMR spectra as those of the product of Example 1.

EXAMPLE 5

In 20 ml of a phosphate buffer solution having a pH value of 6.3 was suspended 1.0 g of the 7β-[D(−)-α-(4-ethyl-2,3-dioxo-1-piperazinylcarbonylamino)-phenylacetamido]-7α-methoxy-3-acetoxymethyl-Δ³-cephem-4-carboxylic acid obtained in Example 1, and 0.28 g of sodium hydrogen carbonate was then added thereto to form a solution. Then, 0.2 g of 1-methyl-5-mercapto-1,2,3,4-tetrazole was added, and the resulting mixture was reacted at 50° C. for 24 hours while keeping its pH value at 6.5–6.7 by use of 20% phosphoric acid and sodium hydrogen carbonate. After the reaction, the reaction mixture was cooled and the pH value thereof was adjusted to 5.0 by adding dilute hydrochloric acid. It was thoroughly washed with ethyl acetate, and the aqueous layer was combined with 20 ml of ethyl acetate and 5 ml of acetone, after which its pH was adjusted to 1.5 by adding dilute hydrochloric acid. The ethyl acetate layer was separated off, thoroughly washed with saturated aqueous solution of sodium chloride and dried over anhydrous magnesium sulfate, after which the solvent was distilled off under reduced pressure. The residue was well dispersed in ethyl ether and collected by filtration. Thus there was obtained, in a crystalline form, 0.72 g (yield 65.9%) of 7β-[D(−)-α-(4-ethyl-2,3-dioxo-1-piperazinylcarbonylamino)-phenylacetamido]-7α-methoxy-3-[5-(1-methyl-1,2,3,4-tetrazolyl)thiomethyl]-Δ³-cephem-4-carboxylic acid melting at 160°–165° C. with decomposition. This product had the same IR and NMR spectra as those of the product of Example 2.

EXAMPLE 6

In 60 ml of anhydrous methylene chloride were dissolved 5.87 g of benzhydryl 7β-(α-phenylacetamido)-7α-methoxy-3-acetoxymethyl-Δ³-cephem-4-carboxylate and 4.2 ml of dimethylaniline. To the solution was added 2.4 g of phosphorus pentachloride at a temperature of −20° to −30° C. and reacted at that temperature for 2 hours. Then 40 ml of methanol was dropped over a period of 30 minutes, while keeping the temperature at −25° to −30° C., and the resulting mixture was reacted at that temperature for an additional 2.5 hours. Subsequently, 6.9 ml of dimethylaniline was added and the resulting mixture was cooled to −20° C. On the other hand, a solution of 3.2 g of D(−)-α-(4-ethyl-2,3-dioxo-1-piperazinylcarbonylamino)phenylacetic acid and 1.27 ml of dimethylaniline in 40 ml of methylene chloride was cooled to a temperature of −20° to −15° C., to which 1.1 g of ethyl chlorocarbonate was added dropwise. The resulting mixture was stirred at that temperature for 1.5 hours, and then cooled to −25° C. The mixture was added to the above-mentioned reaction liquied and the resulting mixture was reacted at a temperature of −20° to −15° C. for 2 hours, then at a temperature of −10° to −5° C. for one hour and further at a temperature of 0° to 5° C. for one hour. After the reaction, the solvent was distilled off under reduced pressure. The residue was dissolved in a mixture of 50 ml of ethyl acetate, 6 ml of acetone and 20 ml of water, and the pH value of the solution was adjusted to 1.5 by adding dilute hydrochloric acid with ice-cooling. The organic layer was separated off, and the aqueous layer was extracted with 10 ml of ethyl acetate. The organic layers were combined, 20 ml of water was added thereto. The pH of the mixture was adjusted to 7.0 with sodium hydrogen carbonate. The organic layer was separated and dried over anhydrous magnesium sulfate, after which the solvent was distilled off under reduced pressure. The residue was purified by means of column chromatography on silica gel with a 1:1 (by volume) mixture of ethyl acetate and benzene as eluant. Thus there was obtained, in a crystalline form, 4.78 g (yield 62%) of benzhydryl 7β-[D(−)-α-(4-ethyl-2,3-dioxo-1-piperazinylcarbonylamino)phenylacetamido]-7α-methoxy-3-acetoxymethyl-Δ³-cephem-4-carboxylate melting at 106°–109° C. with decomposition. This product had the same IR and NMR spectra as those of the product of Example 1.

EXAMPLE 7

In a mixture of 15 ml of water and 10 ml of ethyl acetate was suspended 0.49 g of 7β-D(−)-α-aminophenylacetamido-7α-methoxy-3-[5-(1-methyl-1,2,3,4-tetrazolyl)thiomethyl]-Δ³-cephem-4-carboxylic acid. The pH value of the suspension was adjusted to 7–8 by adding sodium hydrogen carbonate. While cooling the suspension, 0.21 g of 4-ethyl-2,3-dioxo-1-piperazinylcarbonyl chloride was added thereto over a period of 5 minutes, after which the mixture was reacted for 30 minutes while controlling the pH at 7–8 by adding sodium hydrogen carbonate. After the reaction, the aqueous layer was separated off, and washed with 10 ml of ethyl acetate, and 15 ml of ethyl acetate was added thereto. The pH value of the resulting mixture was adjusted to 2.0 with 2 N hydrochloric acid. The ethyl acetate layer was separated off, thoroughly washed with water and dried over anhydrous magnesium sulfate, after which the solvent was distilled off under reduced pressure. Thus there was obtained, in a crystalline form, 0.49 g (yield 74.4%) of 7β-[D(−)-α-(4-ethyl-2,3-dioxo-1-piperazinylcarbonylamino)-phenylacetomido]7α-methoxy-3-[5-(1-methyl-1,2,3,4-tetrazolyl)thiomethyl]Δ³-cephem-4-carboxylic acid melting at 160°–165° C. with decomposition. This product had the same IR and NMR spectra as those of the product of Example 2.

EXAMPLE 8

The following compounds can be obtained according to the substantially same procedures as shown in Examples 1 to 7 by selecting the appropriate starting materials:

7β-[D(−)-α-(4-ethyl-2,3-dioxo-1-piperazinylcarbonylamino)-p-hydroxyphenylacetamido]-7α-methoxy-3-[2-(1,3,4-thiadiazolyl)thiomethyl]-Δ³-cephem-4-carboxylic acid, 7β-[D-(−)-α-(4-ethyl-2,3-dioxo-1-piperazinylcarbonylamino)-p-hydroxyphenylacetamido]-7α-methoxy-3-[2-(1,3,4-triazolyl)thiomethyl]-Δ$^3$-cephem-4-carboxylic acid, 7β-[D(−)-α-(4-ethyl-2,3-dioxo-1-piperazinylcarbonylamino)-p-hydroxyphenylacetamido]-7α-methoxy-3-methoxymethyl-Δ$^3$-cephem-4-carboxylic acid, 7β-[D(−)-α-(4-ethyl-2,3-dioxo-1-piperazinylcarbonylamino)-p-hydroxyphenylacetamido]-7α-methoxy-3-[2-(5-methyl-1,3,4-triazolyl)thiomethyl]-Δ$^3$-cephem-4-carboxylic acid, 7β-[D(−)-α-(4-ethyl-2,3-dioxo-1-piperazinylcarbonylamino)-p-hydroxyphenylacetamido]-7α-methoxy-3-[5-(1,3,4-triazolyl)thiomethyl]-Δ$^3$-cephem-4-carboxylic acid, 7β-[D(−)-α-(4-ethyl-2,3-dioxo-1-piperazinylcarbonylamino)-p-hydroxyphenylacetamido]-7α-methoxy-3-[5-(1,2,3,4-tetrazolyl)thiomethyl]-Δ$^3$-cephem-4-carboxylic acid, 7β-[D(−)-α-(4-ethyl-2,3-dioxo-1-piperazinylcarbonylamino)-p-hydroxyphenylacetamido]-7α-methoxy-3-[2-(5-methyl-1,3,4-oxadiazolyl)thiomethyl]-Δ$^3$-cephem-4-carboxylic acid, 7β-[D(−)-α-(4-ethyl-2,3-dioxo-1-piperazinylcarbonylamino)-p-hydroxyphenylacetamido]-7α-methoxy-3-[2-(4-methylthiazolyl)thiomethyl]-Δ$^3$-cephem-4-carboxylic acid, 7β-[D(−)-α-(4-ethyl-2,3-dioxo-1-piperazinylcarbonylamino)-p-hydroxyphenylacetamido]-7α-methoxy-3-[2-(pyridine-1-oxide)thiomethyl]-Δ$^3$-cephem-4-carboxylic acid, 7β-[D(−)-α-(4-ethyl-2,3-dioxo-1-piperazinylcarbonylamino)-p-hydroxyphenylacetamido]-7α-methoxy-3-[5-(1-ethyl-1,2,3,4-tetrazolyl)thiomethyl]-Δ$^3$-cephem-4-carboxylic acid, 7β-[D(−)-α-(4-ethyl-2,3-dioxo-1-piperazinylcarbonylamino)-p-hydroxyphenylacetamido]-7α-methoxy-3-[3-(2,6-dimethyl-5-oxo-2,5-dihydro-1,2,4-triazinyl)thiomethyl]-Δ$^3$-cephem-4-carboxylic acid, 7β-[D(−)-α-(4-ethyl-2,3-dioxo-1-piperazinylcarbonylamino)-p-hydroxyphenylacetamido]-7α-methoxy-3-[2-(4-methyloxazolyl)thiomethyl]-Δ$^3$-cephem-4-carboxylic acid, 7β-[D(−)-α-(4-ethyl-2,3-dioxo-1-piperazinylcarbonylamino)-p-hydroxyphenylacetamido]-7α-methoxy-3-(2-thiazolinylthiomethyl)-Δ$^3$-cephem-4-carboxylic acid, 7β-[D(−)-α-(4-ethyl-2,3-dioxo-1-piperazinylcarbonylamino)-p-hydroxyphenylacetamido]-7α-methoxy-3-[2-(1-methylimidazolyl)thiomethyl]-Δ$^3$-cephem-4-carboxylic acid, 7β-[D(−)-α-(4-ethyl-2,3-dioxo-1-piperazinylcarbonylamino)-p-hydroxyphenylacetamido]-7α-methoxy-3-[3-(6-methylpyridazinyl)thiomethyl]-Δ$^3$-cephem-4-carboxylic acid, and 7β-[D(−)-α-(4-ethyl-2,3-dioxo-1-piperazinylcarbonylamino)-p-hydroxyphenylacetamido]-7α-methoxy-3-(2-pyrimidinylthiomethyl)-Δ$^3$-cephem-4-carboxylic acid.

EXAMPLE 9

In 30 ml of anisole was dissolved 0.825 g of benzhydryl 7β-[D(−)-α-(4-ethyl-2,3-dioxo-1-piperazinylcarbonylamino)phenylacetamido]-7α-methoxy-3-[5-(1-methyl-1,2,3,4-tetrazolyl)thiomethyl]-Δ$^3$-cephem-4-carboxylate. While cooling the resulting solution with ice, 8 ml of trifluoroacetic acid was added thereto and reacted with the carboxylate at a temperature of 0° to 5° C. for one hour. The reaction liquid was concentrated to dryness under reduced pressure at a temperature below 35° C. The residue was dissolved in 30 ml of 2% aqueous solution of sodium hydrogen carbonate and washed twice with 10 ml portions of ethyl acetate. The water layer was separated, and mixed with 30 ml of fresh ethyl acetate, and the resulting mixture was adjusted to a pH value of 1.5 with 2 N hydrochloric acid. Subsequently, the mixture solution was stirred at room temperature for 2 hours to deposit crystals, which were then filtered and dried to obtain 0.575 g (yield 87.2%) of 7β-[D(−)-α-(4-ethyl-2,3-dioxo-1-piperazinylcarbonylamino)phenylacetamido]-7α-methoxy-3-[5-(1-methyl-1,2,3,4-tetrazolylthiomethyl]-Δ$^3$-cephem-4-carboxylic acid.

EXAMPLE 10

(1) In a mixed solvent of 15 ml of anhydrous tetrahydrofuran and 15 ml of anhydrous methanol was dissolved 0.76 g of benzhydryl 7β-[D(−)-α-(4-ethyl-2,3-dioxo-1-piperazinylcarbonylamino)-p-hydroxyphenylacetamido]-3-acetoxymethyl-Δ$^3$-cephem-4-carboxylate, and the resulting solution was cooled to −75° C., to which 2.8 ml of a solution of lithium methoxide in methanol (5.04 mM of lithium methoxide was contained) was added. The resulting mixture was subjected to reaction for 2 minutes, and thereto was added 0.14 ml of tert.-butyl hypochlorite. The resulting mixture was subjected to reaction for 20 minutes. To the resulting reaction solution were added 0.28 ml of glacial acetic acid and 0.1 ml of triethyl phosphite in this order, after which the temperature of the reaction solution was elevated to room temperature. The reaction solution was concentrated under reduced pressure, and the resulting residue was dissolved in a mixed solvent of 15 ml of water and 20 ml of ethyl acetate. The resulting ethyl acetate layer was separated off, washed with a dilute aqueous solution of sodium hydrogen carbonate, water, and saturated sodium chloride solution in water successively, and then dried on anhydrous magnesium sulfate. The solvent was distilled off under reduced pressure, and the residue was purified by column chromatography on silica gel with a 1:1 (by volume) mixture of ethyl acetate and benzene as eluant, to obtain 0.62 g (yield 78.5%) of benzhydryl 7β-[D(−)-α-(4-ethyl-2,3-dioxo-1-piperazinylcarbonylamino)-p-hydroxyphenylacetamido]-7α-methoxy-3-acetoxymethyl-Δ$^3$-cephem-4-carboxylate.

IR (KBr) cm$^{-1}$: $\nu_{NH}$ 3270; $\nu_{CO}$ 1780, 1670–1710

NMR (d$_6$-DMSO) ppm values: 1.09 (3H, t, —CH$_3$), 1.95 (3H, s, —CH$_3$), 3.25–3.50 (6H, m, >CH$_2$×3), 3.45 (3H, s, —CH$_3$), 3.90 (2H, m, >CH$_2$), 4.85 (2H, q, >CH$_2$), 5.00 (1H, s, >CH), 5.50 (1H, d, >CH), 6.85 (1H, s, >CH), 6.77–7.30 (14H, —C$_6$H$_5$×2 and >C$_6$H$_4$), 7.95 (1H, s, >NH), 9.70 (1H, d, >NH).

(2) To 0.5 g of the benzhydryl ∂β-[D(−)-α-(4-ethyl-2,3-dioxo-1-piperazinylcarbonylamino)-p-hydroxyphenylacetamido]-7α-methoxy-3-acetoxymethyl-Δ$^3$-cephem-4-carbo..ylate obtained in above (1) were added 5 ml of anisole and 5 ml of trifluoroacetic acid, and the resulting mixture was subjected to reaction for one hour with ice-cooling. After the reaction, the reaction solution was concentrated to dryness under reduced pressure. To the residue were added 15 ml of water and 20 ml of ethyl acetate, and then sodium hydrogen carbonate was added thereto to adjust the pH thereof to 7.0, thereby dissolving the residue in the solvent. The resulting aqueous layer was separated off, and 25 ml of fresh ethyl acetate was added thereto, after which 2 N hydrochloric acid was dropped thereinto to adjust the pH thereof to 2.0 with stirring. The resulting ethyl acetate layer was separated off, washed with water and saturated sodium chloride solution in water in this order, and then dried on anhydrous magnesium sulfate. The solvent was then distilled off under reduced pressure to obtain 0.32 g (yield 81.2%) of 7β-[D(—)-α-(4-ethyl-2,3-dioxo-1-piperazinylcarbonylamino)-p-hydroxyphenylacetamido]-7α-methoxy-3-acetoxymethyl-Δ³-cephem-4-carboxylic acid.

NMR (d$_6$-DMSO) ppm values: 1.10 (3H, t, —CH$_3$), 2.00 (3H, s, —CH$_3$), 3.20–3.60 (6H, m, >CH$_2$×3), 3.40 (3H, s, —CH$_3$), 3.90 (2H, m, >CH$_2$), 4.77 (2H, q, >CH$_2$), 5.09 (1H, s, ≫CH), 5.50 (1H, d, ≫CH), 6.65–7.33 (4H, q, >C$_6$H$_4$), 9.63 (2H, >NH×2).

IR (KBr) cm$^{-1}$: $\nu_{C=O}$ 1775, 1720, 1710, 1700, 1675

In the same manner as above, the following compounds were obtained:

7β-[D(—)-α-(4-ethyl-2,3-dioxo-1-piperazinylcarbonylamino)phenylacetamido]-7α-methoxy-3-acetoxymethyl-Δ³-cephem-4-carboxylic acid, IR (KBr) cm$^{-1}$: $\nu_{C=O}$ 1775, 1720, 1705, 1675

7β-[D(—)-α-(4-ethyl-2,3-dioxo-1-piperazinylcarbonylamino)-p-hydroxyphenylacetamido]-7α-methoxy-3-carbamoyloxymethyl-Δ³-cephem-4-carboxylic acid.

EXAMPLE 11

In a mixed solvent of 20 ml of anhydrous tetrahydrofuran and 15 ml of anhydrous methanol was dissolved 0.81 g of benzhydryl 7β-[D(—)-α-(4-ethyl-2,3-dioxo-1-piperazinylcarbonylamino)-p-hydroxyphenylacetamido]-3-[5-(1-methyl-1,2,3,4-tetrazolyl)thiomethyl]-Δ³-cephem-4-carboxylate, and the resulting solution was cooled to —75° C. To the solution was added 2.8 ml of a methanol solution of lithium methoxide (5.04 mM of lithium methoxide was contained), and the resulting mixture was subjected to reaction for 2 minutes, after which 0.14 ml of tert.-butyl hypochlorite was added thereto, and the resulting mixture was subjected to reaction for 15 minutes. To the resulting reaction solution were added 0.28 ml of acetic acid and 0.1 ml of triethyl phosphite in this order, after which the temperature of the reaction solution was elevated to room temperature. The reaction solution was concentrated under reduced pressure, and to the residue were added 15 ml of water and 25 ml of ethyl acetate to dissolve the residue in the solvent, after which the resulting ethyl acetate layer was separated off. The ethyl acetate layer was washed with a dilute aqueous sodium hydrogen carbonate solution, water, and saturated sodium chloride solution in water in this order, and then dried on anhydrous sodium sulfate. The solvent was removed by distillation under reduced pressure, and the residue was purified by means of column chromatography on silica gel with a 1:1 mixture of ethyl acetate and benzene as eluant, to obtain crystals of benzhydryl 7β-[D(—)-α-(4-ethyl-2,3-dioxo-1-piperazinylcarbonylamino)-p-hydroxyphenylacetamido]-7α-methoxy-3-[5-(1-methyl-1,2,3,4-tetrazolyl)thiomethyl]-Δ³-cephem-4-carboxylate. To the crystals were added 4 ml of anisole and 4 ml of trifluoroacetic acid, and the resulting mixture was subjected to reaction with ice-cooling for one hour. After the reaction, the reaction solution was concentrated under reduced pressure to dryness. To the resulting residue were added 10 ml of water and 15 ml of ethyl acetate, and then sodium hydrogen carbonate was added thereto to adjust the pH thereof to 7.0, thereby dissolving the residue in the solvent. The resulting aqueous layer was separated off, and 10 ml of methyl acetate was added to the aqueous layer, after which 2 N hydrochloric acid was dropped thereinto with stirring to adjust the pH thereof to 2.0, and the stirring was continued at room temperature for a period of 2 to 3 hours. The thus deposited crystals were collected by filtration, and then dried to obtain 0.29 g (yield 42.9%) of crystals of 7β-D(—)-α-(4-ethyl-2,3-dioxo-1-piperazinylcarbonylamino)-p-hydroxyphenylacetamido]-7α-methoxy-3-[5-(1-methyl-1,2,3,4-tetrazolyl)thiomethyl]-Δ³-cephem-4-carboxylic acid.

NMR (d$_6$-DMSO) ppm values: 1.06 (3H t, —CH$_3$), 3.35 (3H, s, —CH$_3$), 3.30–3.55 (6H, m, >CH$_2$×3), 3.87 (3H, s, —CH$_3$), 3.90–4.55 (4H, m, >CH$_2$×2), 5.05 (1H, s, ≫CH), 5.50 (1H, d, ≫CH), 6.65–7.35 (4H, q, >C$_6$H$_4$), 9.55–9.70 (2H, >NH×2).

The compound obtained above was neutralized with an aqueous sodium hydrogen carbonate solution to adjust the pH thereof to 7.0, and then subjected to filtration. The resulting filtrate was subjected to lyophilization to obtain the sodium salt of 7β-[D(—)-α-(4-ethyl-2,3-dioxo-1-piperazinylcarbonylamino)-p-hydroxyphenylacetamido]-7α-methoxy-3-[5-(1-methyl-1,2,3,4-tetrazolyl)thiomethyl]-Δ³-cephem-4-carboxylic acid.

In the same manner as above, the following compounds were obtained:

7β-[D(—)-α-(4-ethyl-2,3-dioxo-1-piperazinylcarbonylamino)phenylacetamido]-7α-methoxy-3-[5-(1-methyl-1,2,3,4-tetrazolyl)thiomethyl]-Δ³-cephem-4-carboxylic acid, and 7β-[D(—)-α-(4-ethyl-2,3-dioxo-1-piperazinylcarbonylamino)-p-hydroxyphenylacetamido]-7α-methoxy-3-[2-(5-methyl-1,3,4-thiadiazolyl)thiomethyl]-Δ³-cephem-4-carboxylic acid.

EXAMPLE 12

In a mixed solvent of 20 ml of anhydrous chloroform and 3 ml of anhydrous tetrahydrofuran was dissolved 0.63 g of 7β-[D(—)-α-(4-ethyl-2,3-dioxo-1-piperazinylcarbonylamino)phenylacetamido]-3-[5-(1-methyl-1,2,3,4-tetrazolyl)thiomethyl]-Δ³-cephem-4-carboxylic acid. The resulting solution was cooled to —75° C., and thereto was added 3.16 ml of a methanol solution of lithium methoxide (4.5 mM of lithium methoxide was contained), and the resulting mixture was subjected to reaction for 3 minutes. To the reaction mixture was added 0.18 ml of tert.-butyl hypochlorite, and the resulting mixture was subjected to reaction for 15 minutes. After the reaction, to the reaction solution were added 0.26 ml of acetic acid and 0.1 ml of triethyl phosphite in this order, after which the temperature of the reaction solution was elevated to room temperature. The reaction solution was concentrated under reduced pressure to dryness, and the residue was added to a mixed solvent of 15 ml of ethyl acetate and 15 ml of water, and then sodium hydrogen carbonate was added thereto to adjust the pH thereof to 7.0. The resulting aqueous layer was separated off, and thereto was added 15 ml of methyl acetate, after which 2 N hydrochloric acid was dropped thereinto with stirring to adjust the pH to 2.0, and the resulting solution was allowed to stand overnight in a referegerator. The thus deposited crystals were collected by filtration, washed with water, and methyl acetate in this order, and thereafter dried to obtain 0.36 g (yield 55%) of 7β-[D(—)-α-(4-ethyl-2,3-dioxo-1-piperazinylcarbonylamino)phenylacetamido]-

7α-methoxy-3-[5-(1-methyl-1,2,3,4-tetrazolyl)thiomethyl]-Δ³-cephem-4-carboxylic acid.

In the same manner as above, the following compound was obtained: 7β-[D(−)-α-(4-ethyl-2,3-dioxo-1-piperazinylcarbonylamino)phenylacetamido]-7α-methoxy-3-acetoxymethyl-Δ³-cephem-4-carboxylic acid.

EXAMPLE 13

(1) In a mixed solvent of 20 ml of chloroform and 5 ml of dried tetrahydrofuran was dissolved 0.76 g of diphenylmethyl 7β-[D(−)-α-(4-ethyl-2,3-dioxo-1-piperazinylcarbonylamino)phenylacetamido]-3-n-propylthiomethyl-Δ³-cephem-4-carboxylate [IR (KBr) cm$^{-1}$: $\nu_{C=O}$ 1770, 1705, 1690, 1670], and the resulting solution was cooled to −75° C. in a methanol-dry ice bath. At the same temperature, 3.5 ml of a 1.425 millimoles/ml solution of lithium methoxide in methanol was added thereto, and the resulting solution was stirred for 30 minutes, after which 0.16 ml of tert.-butyl hypochlorite was added thereto. The resulting mixture was stirred at −70° C. for 15 minutes, and thereto were added 0.29 ml of acetic acid and 0.1 ml of triethyl phosphite in this order, after which the temperature of the solution was elevated to room temperature.

The reaction mixture thus obtained was poured into 30 ml of a citric acid buffer solution (pH 7.0), and the organic layer was separated off and washed twice with 20 ml portions of water. To the organic layer was added 20 ml of water, and the pH thereof was adjusted to 2.0 with 2 N hydrochloric acid, after which the organic layer was washed twice with 20 ml portions of water and then dried on magnesium sulfate. The magnesium sulfate was removed by filtration, and the solvent was removed by distillation under reduced pressure. The residue was purified by means of column chromatography on silica gel with a 1:1 mixture of benzene and ethyl acetate as eluant, to obtain 0.43 g (yield 54.4%) of diphenylmethyl 7β-[D(−)-α-(4-ethyl-2,3-dioxo-1-piperazinylcarbonylamino)phenylacetamido]-7α-methoxy-3-n-propylthiomethyl-Δ³-cephem-4-carboxylate.

IR (KBr) cm$^{-1}$: $\nu$C=O 1770, 1705, 1690, 1675

NMR (CDCl₃) ppm values: 0.78–1.20 (6H, m, —CH₃×2), 1.30–1.65 (2H, m, >CH₂), 2.40 (2H, t, >CH₂), 3.25–3.75 (6H, m, >CH₂×3), 3.50 (3H, s, —CH₃), 3.75–4.20 (4H, m, >CH₂×2), 5.00 (1H, s, C₆—H), 5.70 (1H, d, Cα—H),

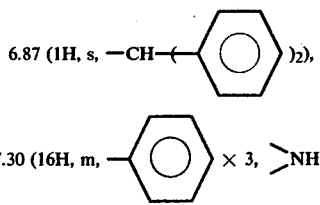

6.87 (1H, s, —CH—(⌬)₂), 7.30 (16H, m, —⌬ × 3, >NH), 7.70 (1H, d, >NH).

(2) In 3 ml of anisole was dissolved 0.30 g of diphenylmethyl 7β-[D(−)-α-(4-ethyl-2,3-dioxo-1-piperazinylcarbonylamino)phenylacetamido]-7α-methoxy-3-n-propylthiomethyl-Δ³-cephem-4-carboxylate, and to the resulting solution was added 2.0 ml of trifluoroacetic acid with ice-cooling and then stirred at the same temperature for 30 minutes. Under reduced pressure, the trifluoroacetic acid and the anisole were distilled off, and the residue was dried to dryness. To the residue was added 5 ml of ethyl acetate, and 6 N hydrochloric acid was then added to adjust the pH thereof to 2.0, after which the organic layer was separated off, and then washed twice with 5-ml portions of water. The organic layer was dried on magnesium sulfate, and the solvent was removed by distillation under reduced pressure, after which the residue was treated with ether to obtain 0.21 g (yield 88.6%) of 7β-[D(−)-α-(4-ethyl-2,3-dioxo-1-piperazinylcarbonylamino)phenylacetamido]-7α-methoxy-3-n-propylthiomethyl-Δ³-cephem-4-carboxylic acid in the white powder form.

IR (KBr) cm$^{-1}$: $\nu_{C=O}$ 1770, 1720, 1705, 1685, 1670

NMR (d₆-DMSO) ppm values: 0.77–1.20 (6H, m, —CH₃×2), 1.30–1.65 (2H, m, >CH₂), 2.40 (2H, t, >CH₂), 3.25–3.75 (6H, m, >CH₂×3), 3.40 (3H, s, —CH₃), 3.80–4.15 (4H, m, >CH₂×2), 5.10 (1H, s, ⋙CH), 5.65 (1H, d, ⋙CH),

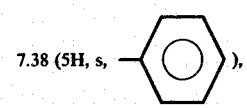

7.38 (5H, s, —⌬), 9.73 (2H, >NH×2).

In the same manner as above, the following compounds were obtained:

7β-(−)-α-(4-ethyl-2,3-dioxo-1-piperazinylcarbonylamino)phenylacetamido]-7α-methoxy-3-methylthiomethyl-Δ³-cephem-4-carboxylic acid, 7β-[D(−)-α-(4-ethyl-2,3-dioxo-1-piperazinylcarbonylamino)phenylacetamido]-7α-methoxy-3-ethylthiomethyl-Δ³-cephem-4-carboxylic acid, 7β-[D(−)-α-(4-ethyl-2,3-dioxo-1-piperazinylcarbonylamino)phenylacetamido]-7α-methoxy-3-n-butylthiomethyl-Δ³-cephem-4-carboxylic acid, 7β-[D(−)-α-(4-ethyl-2,3-dioxo-1-piperazinylcarbonylamino)-p-hydroxyphenylacetamido]-7α-methoxy-3-methylthiomethyl-Δ³-cephem-4-carboxylic acid, 7β-[D(−)-α-(4-ethyl-2,3-dioxo-1-piperazinylcarbonylamino)-p-hydroxyphenylacetamido]-7α-methoxy-3-ethylthiomethyl-Δ³-cephem-4-carboxylic acid, 7β-[D(−)-α-(4-ethyl-2,3-dioxo-1-piperazinylcarbonylamino)-p-hydroxyphenylacetamido]-7α-methoxy-3-n-propylthiomethyl-Δ³-cephem-4-carboxylic acid, and 7β-[D(−)-α-(4-ethyl-2,3-dioxo-1-piperazinylcarbonylamino)-p-hydroxyphenylacetamido]-7α-methoxy-3-n-butylthiomethyl-Δ³-cephem-4-carboxylic acid.

EXAMPLE 14

(1) In the same manner as in Example 13 (1), 0.8 g of diphenylmethyl 7β-[D(−)-α-(4-ethyl-2,3-dioxo-1-1-piperazinylcarbonylamino)phenylacetamido]-3-ethoxycarbonylmethylthiomethyl-Δ³-cephem-4-carboxylate [IR (KBr) cm$^{-1}$: $\nu_{C=O}$ 1770, 1700, 1680, 1670] was reacted and treated, to obtain 0.55 g (66.4%) of diphenylmethyl 7β-[D(−)-α-(4-ethyl-2,3-dioxo-1-piperazinylcarbonylamino)phenylacetamido]-7α-methoxy-3-ethoxycarbonylmethylthiomethyl-Δ³-cephem-4-carboxylate.

IR (KBr) cm$^{-1}$: $\nu_{C=O}$ 1775, 1715, 1700, 1685, 1670

NMR (CDCl₃) ppm values: 0.95–1.24 (6H, m, —CH₃×2), 3.10 (2H, s, >CH₂), 3.28–3.75 (8H, m, >CH₂×4), 3.40 (3H, s, —CH₃), 3.75–4.15 (4H, m, >CH₂×2), 4.95 (1H, s, ⋙CH), 5.50 (1H, d, ⋙CH), 6.90 (1H, s, ⋙CH), 7.35 (16H, m, 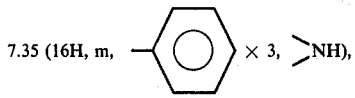 × 3, >NH), 7.70 (1H, d, >NH).

(2) In the same manner as in Example 13 (2), 0.50 g of diphenylmethyl 7β-[D(—)-α-(4-ethyl-2,3-dioxo-1-piperazinylcarbonylamino)phenylacetamido]-7α-methoxy-3-ethoxycarbonylmethylthiomethyl-Δ³-cephem-4-carboxylate was reacted and treated, to obtain 0.35 g (yield 87.5%) of 7β-[D(—)-α-(4-ethyl-2,3-dioxo-1-piperazinylcarbonylamino)phenylacetamido]-7α-methoxy-3-ethoxycarbonylmethylthiomethyl-Δ³-cephem-4-carboxylic acid.

IR (KBr) cm$^{-1}$: $\nu_{C=O}$ 1770, 1715, 1700, 1680, 1670
NMR (d$_6$-DMSO) ppm values: 0.98–1.27 (6H, m, —CH$_3$×2), 3.29–3.78 (10H, m, >CH$_2$×5), 3.41 (3H, s, —CH$_3$), 3.78–4.20 (4H, m, >CH$_2$×2), 5.08 (1H, s, ≫CH), 5.62 (1H, d, ≫CH), 7.40 (5H, s, 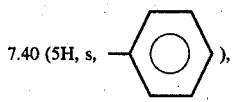 ), 9.72–9.80 (2H, m, >NH×2).

In the same manner as above, the following compound was obtained:

7β-[D(—)-α-(4-ethyl-2,3-dioxo-1-piperazinylcarbonylamino)-p-hydroxyphenylacetamido]-7α-methoxy-3-ethoxycarbonylmethylthiomethyl-Δ³-cephem-4-carboxylic acid.

EXAMPLE 15

(1) In the same manner as in Example 13 (1), 1.42 g of diphenylmethyl 7β-[D(—)-α-(4-ethyl-2,3-dioxo-1-piperazinylcarbonylamino)phenylacetamido]-3-diphenylmethoxycarbonylmethylthiomethyl-Δ³-cephem-4-carboxylate [IR (KBr) cm$^{-1}$: $\nu_{C=O}$ 1775, 1710, 1680, 1670] was reacted and treated, to obtain 1.0 g (yield 68.5%) of diphenylmethyl 7β-[D(—)-α-(4-ethyl-2,3-dioxo-1-piperazinylcarbonylamino)-phenylacetamido]-7α-methoxy-3-diphenylmethoxycarbonylmethylthiomethyl-Δ³-cephem-4-carboxylate.

IR (KBr) cm$^{-1}$: $\nu_{C=O}$ 1780, 1715, 1705, 1695, 1680
NMR (CDCl$_3$) ppm values: 1.08 (3H, t, —CH$_3$), 3.00 (2H, s, >CH$_2$), 3.16 (2H, s, >CH$_2$), 3.43 (3H, s, —CH$_3$), 3.25–3.70 (4H, m, >CH$_2$×2), 3.70–4.10 (4H, m, >CH$_2$×2), 4.90 (1H, s, ≫CH), 5.60 (1H, d, ≫CH), 6.73 (2H, m, ≫CH×2), 7.20 (25H, m, 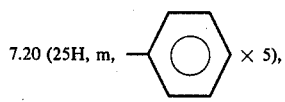 × 5), 7.75 (1H, br, >NH), 9.85 (1H, d, >NH).

(2) In the same manner as in Example 13 (2), 1.0 g of diphenylmethyl 7β-[D(—)-α-(4-ethyl-2,3-dioxo-1-piperazinylcarbonylamino)phenylacetamido]-7α-methoxy-3-diphenylmethoxycarbonylmethylthiomethyl-Δ³-cephem-4-carboxylate was reacted and treated, to obtain 0.58 g (yield 87.9%) of 7β-[D(—)-α-(4-ethyl-2,3-dioxo-1-piperazinylcarbonylamino)phenylacetamido]-7α-methoxy-3-carboxymethylthiomethyl-Δ³-cephem-4-carboxylic acid.

IR(KBr) cm$^{-1}$: $\nu_{C=O}$ 1770, 1715, 1700, 1690, 1670
NMR d$_6$-DMSO) ppm values: 1.13 (3H, t, —CH$_3$), 3.05–3.80 (8H, m, >CH$_2$×4), 3.40 (3H, s, —CH$_3$), 3.80–4.10 (4H, m, >CH$_2$×2), 5.00 (1H, s, ≫CH), 5.55 (1H, d, ≫CH), 7.34 (5H, s, 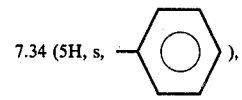 ), 9.70 (2H, m, >NH×2).

In the same manner as above, the following compound was obtained:

7β-[D(—)-α-(4-ethyl-2,3-dioxo-1-piperazinyl carbonylamino)-p-hydroxyphenylacetamido]-7α-methoxy-3-carboxymethylthiomethyl-Δ³-cephem-4-carboxylic acid.

What is claimed is:

1. A 7α-methoxy-cephalosporin represented by the formula:

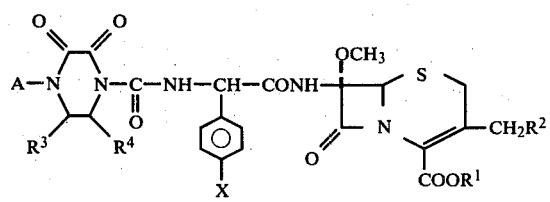

wherein R$^1$ is a hydrogen atom or a pharmaceutically acceptable salt-forming cation; R$^2$ is a substituted or unsubstituted heterocyclic thio group in which the thio linkage is attached to a carbon atom of a 5 or 6 membered aromatic heterocyclic ring composed of carbon and at least one hetero atom selected from oxygen, sulfur and nitrogen, the heterocyclic moiety of said heterocyclic thio group being composed of said aromatic heterocyclic ring or of said aromatic heterocyclic ring fused to a benzene ring or being triazolopyridyl or purinyl, there being up to three substituents in the substituted group, the substituents being selected from halogen, hydroxyl, alkyl having 1 to 13 carbon atoms, alkyloxy having 1 to 5 carbon atoms, hydroxyalkyl having 1 to 5 carbon atoms, alkylthio having 1 to 5 carbon atoms, alkylamino having 1 to 5 carbon atoms, dialkylamino having 1 to 5 carbon atoms in each alkyl, alkanoyl-amino having 2 to 5 carbon atoms, alkanoyl having 2 to 5 carbon atoms, alkanoyloxy having 2 to 5 carbon atoms, N,N-dialkylaminoalkyl having 1 to 5 carbon atoms in each alkyl, alkyloxyalkyl having 1 to 5 carbon atoms in each alkyl, carboxyalkyl having 2 to 6 carbon atoms, sulfoalkyl having 1 to 5 carbon atoms, sulfamoylalkyl having 1 to 5 carbon atoms, carbamoylalkyl having 1 to 5 carbon atoms, phenyl, naphthyl, nitro,, cyano, carboxyl, carbamoyl, sulfo, sulfamoyl and oxo; R$^3$ and R$^4$ are independently a hydrogen atom or a lower alkyl group; A is a singly substituted or unsubstituted alkyl group having 1 to 13 carbon atoms, the substituent on said substituted alkyl group being selected from halogen, hydroxyl, alkyloxy having 1 to 5 carbon atoms, alkylthio having 1 to 5 carbon atoms, nitro, cyano, carboxyl and alkanoyl having 2 to 5 carbon atoms; and X is a hydrogen atom or a hydroxyl group.

2. The 7α-methoxy-cephalosporin according to claim 1, wherein $R^2$ is a substituted or unsubstituted heterocyclic thio group, said substituents of the substituted group being as defined in claim 1 and said heterocyclic thio group being selected from oxazolylthio, thiazolylthio, isoxazolylthio, isothiazolylthio, imidazolylthio, pyrazolylthio, pyridylthio, pyrazinylthio, pyrimidinylthio, pyridazinylthio, quinolylthio, isoquinolylthio, quinazolylthio, indolylthio, indazolylthio, oxadiazolylthio, thiadiazolylthio, triazolylthio, tetrazolylthio, triazinylthio, benzimidazolylthio, benzoxazolylthio, benzthiazolylthio, triazolopyridylthio, purinylthio and pyridine-1-oxide-2-ylthio.

3. The 7α-methoxy-cephalosporin according to claim 1, wherein $R^2$ is a 5-(1-methyl-1,2,3,4-tetrazolyl)thio, 2-(5-methyl-1,3,4-thiadiazolyl)thio, 5-(1,2,3-triazolyl)thio, 5-(1,2,3,4-tetrazolyl)thio, or 2-(1,3,4-thiadiazolyl)thio; $R^3$ is a hydrogen atom; $R^4$ is a hydrogen atom or a lower alkyl group; and A is a lower alkyl group.

4. The 7α-methoxy-cephalosporin according to claim 3, wherein $R^2$ is 5-(1-methyl-1,2,3,4-tetrazolyl)thio, or 2-(5-methyl-1,3,4-thiadiazolyl)thio; $R^4$ is a hydrogen atom; and A is methyl or ethyl.

5. The 7α-methoxy-cephalosporin according to claim 4, wherein A is ethyl.

6. The 7α-methoxy-cephalosporin according to claim 5, wherein X is hydroxyl.

7. The 7α-methoxy-cephalosporin according to claim 5, wherein X is hydrogen.

8. 7β-[D(−)-α-(4-ethyl-2,3-dioxo-1-piperazinylcarbonylamino)phenylacetamido]-7α-methoxy-3-[5-(1-methyl-1,2,3,4-tetrazolyl)thiomethyl]-Δ³-cephem-4-carboxylic acid or its non-toxic salt.

9. 7β-[D(−)-α-(4-ethyl-2,3-dioxo-1-piperazinylcarbonylamino)-p-hydroxyphenylacetamido]-7α-methoxy-3-[5-(1-methyl-1,2,3,4-tetrazolyl)thiomethyl]-Δ³-cephem-4-carboxylic acid or its non-toxic salt.

10. 7β-[D(−)-α-(4-ethyl-2,3-dioxo-1-piperazinylcarbonylamino)phenylacetamido]-7α-methoxy-3-[2-(5-methyl-1,3,4-thiadiazolyl)thiomethyl]-Δ³-cephem-4-carboxylic acid or its non-toxic salt.

11. 7β-[D(−)-α-(4-ethyl-2,3-dioxo-1-piperazinylcarbonylamino)-p-hydroxyphenylacetamido]-7α-methoxy-3-[2-(5-methyl-1,3,4-thiadiazolyl)thiomethyl]-Δ³-cephem-4-carboxylic acid or its non-toxic salt.

12. A 7α-methoxy-cephalosporin represented by the formula:

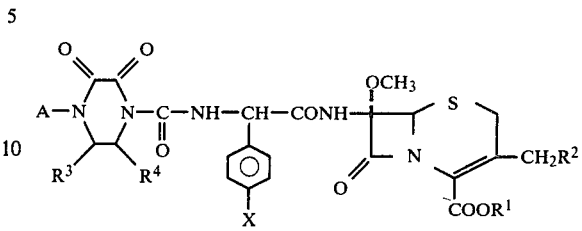

wherein $R^1$ is a protective group; $R^2$ is a substituted or unsubstituted heterocyclic thio group in which the thio linkage is attached to a carbon atom of a 5 or 6 membered aromatic heterocyclic ring composed of carbon and at least one hetero atom selected from oxygen, sulfur or nitrogen, the heterocyclic moiety of said heterocyclic thio group being composed of said aromatic heterocyclic ring or of said aromatic heterocyclic ring fused to a benzene ring or being triazolopyridyl or purinyl, there being up to three substituents in the substituted group, the substituents being selected from halogen, hydroxyl, alkyl having 1 to 13 carbon atoms, alkyloxy having 1 to 5 carbon atoms, hydroxyalkyl having 1 to 5 carbon atoms, alkylthio having 1 to 5 carbon atoms, alkylamino having 1 to 5 carbon atoms, dialkylamino having 1 to 5 carbon atoms in each alkyl, alkanoyl amino having 2 to 5 atoms, alkanoyl having 2 to 5 carbon atoms, alkanoyloxy having 2 to 5 carbon atoms, N,N-dialkylaminoalkyl having 1 to 5 carbon atoms in each alkyl, alkyloxyalkyl having 1 to 5 carbon atoms in each alkyl, carboxyalkyl having 2 to 6 carbon atoms, sulfoalkyl having 1 to 5 carbon atoms, sulfamoylalkyl having 1 to 5 carbon atoms, carbamoylalkyl having 1 to 5 carbon atoms, phenyl, naphthyl, nitro, cyano, carboxyl, carbamoyl, sulfo, sulfamoyl and oxo; $R^3$ and $R^4$ are independently a hydrogen atom or a lower alkyl group; A is a singly substituted or unsubstituted alkyl group having 1 to 13 carbon atoms, the substituent on said substituted alkyl group being selected from halogen, hydroxyl, alkyloxy having 1 to 5 carbon atoms, alkylthio having 1 to 5 carbon atoms, nitro, cyano, carboxyl and alkanoyl having 2 to 5 carbon atoms; and X is a hydrogen atom or a hydroxyl group.

* * * * *

UNITED STATES PATENT AND TRADEMARK OFFICE
CERTIFICATE OF CORRECTION

PATENT NO. : 4,200,744
DATED : April 29, 1980
INVENTOR(S) : Isamu Saikawa et al.

It is certified that error appears in the above—identified patent and that said Letters Patent is hereby corrected as shown below:

On the title page, the second to last inventor's name "Masuru Tai" should read -- Masaru Tai --.

In the Foreign Application Priority Data, the following should be added:

-- Jan. 22, 1976      Japan ............51-6117 --.

Signed and Sealed this

Ninth Day of September 1980

[SEAL]

Attest:

SIDNEY A. DIAMOND

Attesting Officer

Commissioner of Patents and Trademarks